United States Patent
Nikkhah et al.

(10) Patent No.: US 10,712,339 B2
(45) Date of Patent: Jul. 14, 2020

(54) ENGINEERING OF A NOVEL BREAST TUMOR MICROENVIRONMENT ON A MICROFLUIDIC CHIP

(71) Applicants: Mehdi Nikkhah, Scottsdale, AZ (US); Danh Truong, Tempe, AZ (US)

(72) Inventors: Mehdi Nikkhah, Scottsdale, AZ (US); Danh Truong, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 457 days.

(21) Appl. No.: 15/730,335

(22) Filed: Oct. 11, 2017

(65) Prior Publication Data

US 2018/0052151 A1 Feb. 22, 2018

Related U.S. Application Data

(63) Continuation-in-part of application No. 14/872,920, filed on Oct. 1, 2015, now Pat. No. 10,017,724.
(Continued)

(51) Int. Cl.
*B01L 3/00* (2006.01)
*G01N 33/50* (2006.01)
(Continued)

(52) U.S. Cl.
CPC .... *G01N 33/5011* (2013.01); *B01L 3/502707* (2013.01); *B01L 3/502715* (2013.01);
(Continued)

(58) Field of Classification Search
CPC ......... B01L 2300/0816; B01L 2300/12; B01L 3/502707; B01L 3/502715; C12M 23/16; C12M 25/14; G01N 33/5011
See application file for complete search history.

(56) References Cited

U.S. PATENT DOCUMENTS 9,261,496 B2   2/2016 Kamm et al.
2008/0102478 A1 5/2008 Li et al.
(Continued)

FOREIGN PATENT DOCUMENTS

WO   2012050981 A1   4/2012

OTHER PUBLICATIONS

Vickerman, et al., "Design, fabrication and implementation of a novel multi-parameter control microfluidic platform for three-dimensional cell culture and real-time imaging", Lab Chip, 2008, 8(9):1468-1477.
(Continued)

*Primary Examiner* — Jennifer Wecker
(74) *Attorney, Agent, or Firm* — Quarles & Brady LLP

(57) ABSTRACT

A microfluidic device for more accurately modeling the in vitro environment in which cancer occurs is disclosed. The microfluidic device includes a surface defining one or more microfluidic channels, a first three dimensional scaffold comprising one or more cancer cells that is spatially separated from the one or more microfluidic channels, a second three dimensional scaffold, at least a portion of which is contacting and in fluid communication with the first three dimensional scaffold, and that is spatially separated from the one or more microfluidic channels, and a third three dimensional scaffold, at least a portion of which is contacting and in fluid communication with the one or more microfluidic channels and the second three dimensional scaffold. The device can be used to assay anti-cancer agents, or as a system for modeling the growth, behavior, or metastasis and tumor formation of cancer cells.

24 Claims, 18 Drawing Sheets
(13 of 18 Drawing Sheet(s) Filed in Color)

Related U.S. Application Data

(60) Provisional application No. 62/058,186, filed on Oct. 1, 2014.

(51) Int. Cl.
    *C12M 1/00*           (2006.01)
    *C12M 3/00*           (2006.01)
    *C12M 3/06*           (2006.01)
    *C12M 1/12*           (2006.01)

(52) U.S. Cl.
    CPC ............ *C12M 23/16* (2013.01); *C12M 25/14* (2013.01); *B01L 2300/0816* (2013.01); *B01L 2300/12* (2013.01)

(56) References Cited

U.S. PATENT DOCUMENTS

| | | | |
|---|---|---|---|
| 2011/0159522 A1* | 6/2011 | Kamm | C12Q 1/02 435/7.21 |
| 2011/0186165 A1 | 8/2011 | Borenstein et al. | |
| 2014/0057311 A1* | 2/2014 | Kamm | C12M 23/16 435/29 |
| 2014/0273223 A1 | 9/2014 | Cho et al. | |
| 2015/0087006 A1 | 3/2015 | Pak et al. | |
| 2017/0067025 A1 | 3/2017 | Nikkhah et al. | |

OTHER PUBLICATIONS

Chung, et al., "Cell migration into scaffolds under co-culture conditions in a microfluidic platform", Lab Chip, 2009, 9:269-275.
Sudo, et al., "Transport-mediated angiogenesis in 3D epithelial coculture", The FASEB Journal, 2009, 23 (7):2155-2164.
Farahat, et al., "Ensemble Analysis of Angiogenic Growth in Three-Dimensional Microfluidic Cell Cultures", PLoS ONE, 2012, 7(5):e37333, pp. 1-14.
Zervantonakis, et al., "Three-dimensional microfluidic model for tumor cell intravasation and endothelial barrier function", PNAS, 2012, 109(34):13515-13520.
Kalchman, et al., "A three-dimensional microfluidic tumor cell migration assay to screen the effect of anti-migratory drugs and interstitial flow", Microfluid Nanofluid, 2013, 14:969-981.
Jeon, et al., "In Vitro Model of Tumor Cell Extravasation", PLoS ONE, 2013, 8(2):e56910, pp. 1-9.
Chen, et al., "Mechanisms of tumor cell extravasation in an in vitro microvascular network platform", Integr. Biol., 2013, 5:1262-1271.
Bersini, et al., "A microfluidic 3D in vitro model for specificity of breast cancer metastasis to bone", Biomaterials, 2014, 35:2454-2461.
Shin, et al., "Extracellular Matrix Heterogeneity Regulates Three-Dimensional Morphologies of Breast Adenocarcinoma Cell Invasion", Adv. Healthcare Mater., 2013, 2:790-794.
Polacheck, et al., "Interstitial flow influences direction of tumor cell migration through competing mechanisms", PNAS, 2011, 108(27):11115-11120.
Au, P. et al., "Paradoxical Effects of PDGF-BB Overexpression in Endothelial Cells on Engineered Blood Vessels In Vivo", The American Journal of Pathology, Jul. 2009, 175(1), pp. 294-302.
Bosman, F. et al., "Functional structure and composition of the extracellular matrix", The Journal of Pathology, Jul. 2003, 200(4), pp. 423-428.
Bray, J. et al., "Multi-parametric hydrogels support 3D in vitro bioengineered microenvironment models of tumour angiogenesis", Biomaterials, Jun. 2015 (available online Mar. 2015), vol. 53. pp. 609-620.
Bussolino, F. et al., "Hepatocyte growth factor is a potent angiogenic factor which stimulates endothelial cell motility and growth", The Journal of Cell Biology, Nov. 1992, 119(3), pp. 629-641.
Cai, L. et al., "Tumor-associated lymphatic endothelial cell promotes invasion of cervical cancer cells", APMIS: Journal of Pathology Microbiology and Immunology, Dec. 2013 (available online Apr. 2013), 121(12), pp. 1162-1168.
Chen, M. et al., "On-chip human microvasculature assay for visualization and quantification of tumor cell extravasation dynamics", Nature Protocols, May 2017 (available online Mar. 2017), 12(5), pp. 865-880.
Chen, X. et al., "Prevascularization of a fibrin-based tissue construct accelerates the formation of functional anastomosis with host vasculature", Tissue Engineering: Part A, Jun. 2009 (available online Oct. 2008), 15(6), pp. 1363-1371.
Doillon, C. et al., Three-dimensional Culture Systems as a Model for Studying Cancer Cell Invasion Capacity and Anticancer Drug Sensitivity, Jul.-Aug. 2004, 24(4), pp. 2169-2178.
Dvorak, H et al., "Fibrin Containing Gels Induce Angiogenesis", Laboratory Investigation, Dec. 1987, 57(6), pp. 673-686.
Ehsan, S. et al., "A three-dimensional in vitro model of tumor cell intravasation", Integrative Biology, Jun. 2014 (first published Apr. 2014), 6(6), pp. 603-610.
Feng, X. et al., "Fibrin and Collagen Differentially but Synergistically Regulate Sprout Angiogenesis of Human Dermal Microvascular Endothelial Cells in 3-Dimensional Matrix", International Journal of Cell Biology, Apr. 2013, vol. 2013, article ID 231279, 11 pages, doi:10.1155/2013/231279.
Griffith, L. et al., "Capturing complex 3D tissue physiology in vitro", Nature Reviews Molecular Cell Biology, Mar. 2006, vol. 7, pp. 211-224.
Hanahan, D. et al., "Patterns and Emerging Mechanisms of the Angiogenic Switch during Tumorigenesis", Cell, Aug. 1996, 86(3), 353-364.
Hanahan, D. et al., "Hallmarks of Cancer: The Next Generation", Cell, Mar. 2011, 144(5), pp. 646-674.
Huang, W. et al., "Placenta growth factor promotes migration through regulating epithelial-mesenchymal transition-related protein expression in cervical cancer", International Journal of Clinical & Experimental Pathology, Dec. 2014, 7(12), pp. 8506-8519.
Ingthorsson, S. et al., "Endothelial cells stimulate growth of normal and cancerous breast epithelial cells in 3D culture", BMC Research Notes, Jul. 2010, vol. 3, 184, 12 pages, https://doi.org/10.1186/1756-0500-3-184.
Jeon, J. et al., "Human 3D vascularized organotypic microfluidic assays to study breast cancer cell extravasation", Proceedings of the National Academic of Sciences of the USA, Jan. 2015 (available online Dec. 2014), 112(1), pp. 214-219.
Kenig, S. et al., "Glioblastoma and endothelial cells cross-talk, mediated by SDF-1, enhances tumour invasion and endothelial proliferation by increasing expression of cathepsins B, S, and MMP-9", Cancer Letters, Mar. 2010 (available online Aug. 2009), 289(1), pp. 53-61.
Kim, J. et al., "Engineering of a Biomimetic Pericyte-Covered 3D Microvascular Network", Public Library of Science (PLOS) One, Jul. 2015, 10(7), e0133880, 15 pages, doi:10.1371/journal.pone.013388.
Kim, S. et al., "Engineering of functional, perfusable 3D microvascular networks on a chip", Lab on a Chip, Apr. 2013 (first published Jan. 2013), 13(8), pp. 1489-1500.
Kim, S.-A. et al., "Co-culture of 3D tumor spheroids with fibroblasts as a model for epithelial-mesenchymal transition in vitro", Experimental Cell Research, Jul. 2015 (available online May 2015), 335(2), pp. 187-196.
Kimlin, L. et al., "In vitro three-dimensional (3D) models in cancer research: An update", Molecular Carcinogenesis, 2013 (available online Dec. 2011), 52(3), pp. 167-182.
Lee, H. et al., "A microfluidic platform for quantitative analysis of cancer angiogenesis and intravasation", Biomicrofluidics, Sep. 2014, 8(5), 054102, 12 pages, doi:10.1063/1.4894595.
Lee, W.-S. et al., "Myeloid cell leukemia-1 is associated with tumor progression by inhibiting apoptosis and enhancing angiogenesis in colorectal cancer", American Journal of Cancer Research, Jan. 2015 (available online Dec. 2014), 5(1), pp. 101-113.
Lyng, H. et al., "Measurement of cell density and necrotic fraction in human melanoma xenografts by diffusion weighted magnetic resonance imaging", Magnetic Resonance in Medicine, Jun. 2000, 43(6), pp. 828-836.

(56) References Cited

OTHER PUBLICATIONS

Mathur, P. et al., "Relationship between tumour vascularity and circulating cancer cells in patients with colorectal carcinoma", European Journal of Surgical Oncology, Jun. 2001, 27(4), pp. 354-358.

Mierke, C. et al., "Cancer cells regulate biomechanical properties of human microvascular endothelial cells", Journal of Biological Chemistry, Nov. 2011 (available online Sep. 2011), 286(46), pp. 40025-40037.

Migrino, R. et al., "Amyloidogenic medin induces endothelial dysfunction and vascular inflammation through the receptor for advanced glycation endproducts", Cardiovascular Research, Sep. 2017 (available online Jul. 2017), 113(11), pp. 1389-1402.

Nagy, J. et al., "Vascular permeability, vascular hyperpermeability and angiogenesis", Angiogenesis, Jun. 2008 (available online Feb. 2008), 11(2), pp. 109-119.

Nikkhah, M et al., "Cytoskeletal role in differential adhesion patterns of normal fibroblasts and breast cancer cells inside silicon microenvironments", Biomedical Microdevices, Jun. 2009 (available online Dec. 2008), 11(3), pp. 585-595.

Nikkhah, M. et al., "Directed endothelial cell morphogenesis in micropatterned gelatin methacrylate hydrogels", Biomaterials, Dec. 2012 (available online Sep. 2012), 33(35), pp. 9009-9018.

Nikkhah, M. et al., "MCF10A and MDA-MB-231 human breast basal epithelial cell co-culture in silicon micro-arrays", Biomaterials, Oct. 2011 (available online Jul. 2011), 32(30), pp. 7625-7632.

Nikkhah, M. et al., "The cytoskeletal organization of breast carcinoma and fibroblast cells inside three dimensional (3-D) isotropic silicon microstructures", Biomaterials, Jun. 2010 (available online Mar. 2010), 31(16), pp. 4552-4561.

Nishida, N. et al., "Angiogenesis in Cancer", Vascular Health and Risk Management, Sep. 2006, 2(3), pp. 213-219.

Peela, N. et al., "Advanced biomaterials and microengineering technologies to recapitulate the stepwise process of cancer metastasis", Biomaterials, Jul. 2017 (Apr. 2017), vol. 133, pp. 176-207.

Peela, N. et al., "Evaluation of anti-cancer drug Suberoylanilide Hydroxamic Acid (SAHA) on cancer cell phenotype in a three-dimensional (3D) breast tumor-stroma platform", 20th International Conference on Miniaturized Systems for Chemistry and Life Sciences, MicroTAS 2016, Oct. 9-13, 2016, Dublin, Ireland, pp. 565-566.

Peng, H.-H. et al., "Systemic Analysis of Tumor Cell-Induced Endothelial Calcium Signaling and Junction Disassembly", Cellular and Molecular Bioengineering, Sep. 2009 (available online Jul. 2009), 2(3), pp. 375-385.

Potente, M. et al., "Basic and therapeutic aspects of angiogenesis", Cell, Sep. 2011, 146(6), pp. 873-887.

Ren, Y. et al., "Hepatocyte Growth Factor Promotes Cancer Cell Migration and Angiogenic Factors Expression: A Prognostic Marker of Human Esophageal Squamous Cell Carcinomas", Clinical Cancer Research, Sep. 2005, 11(17), pp. 6190-6197.

Ribatti, D., From the discovery of Vascular Endothelial Growth Factor to the introduction of Avastin in clinical trials—an interview with Napoleone Ferrara, The International Journal of Developmental Biology, Jul. 2011, 55(4-5), pp. 383-388.

Rosano, L et al., "Endothelin 1 in cancer: biological implications and therapeutic opportunities", Nature Reviews Cancer, Jul. 2013, vol. 13, 637-651.

Schillaci, O. et al., "Exosomes from metastatic cancer cells transfer amoeboid phenotype to non-metastatic cells and increase endothelial permeability: their emerging role in tumor heterogeneity", Scientifc Reports, Jul. 2017, vol. 7, 4711, 15 pages, doi:10.1038/s41598-017-05002-y.

Sobrino, A. et al., "3D microtumors in vitro supported by perfused vascular networks", Scientific Reports, Aug. 2016, vol. 6, 31589, 11 pages, doi:10.1038/srep31589.

Strobl, J. et al., "Actions of the anti-cancer drug suberoylanilide hydroxamic acid (SAHA) on human breast cancer cytoarchitecture in silicon microstructures", Biomaterials, Sep. 2010 (available online Jun. 2010), 31(27), pp. 7043-7050.

Truong, D. et al., Breast Cancer Cell Invasion into a Three Dimensional Tumor-Stroma Microenvironment, Scientific Reports, Sep. 2016, vol. 6, article No. 34094, 18 pages, doi:10.1038/srep34094.

Van Duinen, V. et al., "Microfluidic 3D cell culture: from tools to tissue models", Current Opinion in Biotechnology, Dec. 2015 (available online Jun. 2015), vol. 35, pp. 118-126.

Versaevel, M. et al., "Spatial coordination between cell and nuclear shape within micropatterned endothelial cells", Nature Communications, Feb. 2012, vol. 3, article No. 671, 11 pages, doi:10.1038/ncomms1668.

Weigelt, B. et al., "The need for complex 3D culture models to unravel novel pathways and identify accurate biomarkers in breast cancer", Advanced Drug Delivery Reviews, Apr. 2014 (available online Jan. 2014), vol. 69-70, pp. 42-51.

Weis, S. et al., "Endothelial barrier disruption by VEGF-mediated Src activity potentiates tumor cell extravasation and metastasis", The Journal of Cell Biology, Oct. 2004, 167(2), pp. 223-229.

Yang, K. et al., "Recapitulation of in vivo-like paracrine signals of human mesenchymal stem cells for functional neuronal differentiation of human neural stem cells in a 3D microfluidic system", Biomaterials, Sep. 2015 (available online Jun. 2015), vol. 63, pp. 177-188.

Yu, Y. et al., "Radiation-induced senescence in securin-deficient cancer cells promotes cell invasion involving the IL-6/STAT3 and PDGF-BB/PDGFR pathways", Scientific Reports, Apr. 2013, vol. 3, 1675, 11 pages, doi:10.1038/srep01675.

Zeng, Q. et al., "Crosstalk between tumor and endothelial cells promotes tumor angiogenesis by MAPK activation of Notch signaling", Cancer Cell, Jul. 2005, 8(1), pp. 13-23.

\* cited by examiner

| | + MDA / + HUVECs | − MDA / + HUVECs | + MDA / − HUVECs |
|---|---|---|---|
| Angiogenin | 480.1 ± 182.2 | 411.7 ± 46.9 | 67.1 ± 17.7 |
| ANG-2 | 582.1 ± 306.2 | 982.5 ± 421.4 | 42.6 ± 46.1 |
| HGF | 236.7 ± 60.1 | 275.5 ± 61.8 | 24.4 ± 32.9 |
| PDGF-BB | 22.2 ± 2.5 | 17.6 ± 3.8 | 1.0 ± 0.6 |
| PlGF | 334.8 ± 54.4 | 403.2 ± 213.4 | 2.5 ± 5.9 |
| EGF | 544.3 ± 230.3 | 517.3 ± 198.1 | 533.1 ± 201.7 |
| bFGF | 760.8 ± 89.4 | 515.0 ± 67.5 | 580.1 ± 209.0 |
| HB-EGF | 5.8 ± 5.7 | 6.1 ± 2.8 | 6.2 ± 4.3 |
| Leptin | 133.2 ± 59.6 | 106.0 ± 34.4 | 142.9 ± 67.7 |
| VEGF | 5363.6 ± 1434.3 | 4870.3 ± 1750.4 | 5065.4 ± 1918.2 |

Fig. 16

ENGINEERING OF A NOVEL BREAST TUMOR MICROENVIRONMENT ON A MICROFLUIDIC CHIP

CROSS-REFERENCE TO RELATED APPLICATIONS

This application is a continuation-in-part of U.S. patent application Ser. No. 14/872,920 filed Oct. 1, 2015 which claims the benefit of U.S. provisional Application No. 62/058,186 filed on Oct. 1, 2014, which are incorporated by reference herein in their entirety.

STATEMENT REGARDING FEDERALLY SPONSORED RESEARCH OR DEVELOPMENT

Not applicable.

BACKGROUND

Metastasis, a process where cancer cells migrate to distant organs from the primary tumor site, is the key biological process responsible for 90% of all cancer related deaths. Metastatic dissemination of cancer cells is a multi-step biological process initiated by tumor angiogenesis and invasion of the cancer cells through their surrounding stroma toward the blood vessels.

Tumor stroma is a structurally complex microenvironment hosting several cell types including endothelial cells (ECs), fibroblasts (FBs) and macrophages, packed in extracellular matrix (ECM), along with a dense network of capillaries. In this respect, the reciprocal interactions of the cancer cells with the surrounding microenvironment significantly influence their malignancy. Therefore, investigation of metastatic behavior of cancer cells in response to various microenvironmental stimuli is the key factor to identify efficient therapeutic strategies.

In the past few years, significant efforts have been devoted toward studying the mechanism of cancer metastasis, using in vivo and in vitro models. Genetically modified animal models have been crucially important to define the molecular basis of disease progression. However, using these models, there are certain difficulties to independently study the effects of various microenvironmental cues (i.e., cell-cell communication, mechanical properties of the matrix) on cancer cells metastasis. Furthermore, extensive testing of therapeutic compounds using in vivo models is a costly process.

Alternatively, in vitro assays have been widely used to study cancer cells behaviors (i.e. migration) within well-controlled experimental conditions. In vitro cell migration studies have been typically performed using 2D rigid substrates, Boyden chambers and transwell-based assays. Although these assays have facilitated high throughput and economically efficient experimental analysis, they do not fully recapitulate the complexities of the native 3D tumor microenvironment.

On the other hand, 3D macroscale ECM hydrogels and scaffolds (i.e. collagen) have shown a great promise for conducting fundamental research in cancer biology. Interestingly, such studies have demonstrated similar drug resistance profiles to those demonstrated by in vivo models. The limiting aspects of 3D macroscale hydrogel models are the lack of precise control over cellular distribution, lack of vascularity and difficulties in establishing stable chemical gradients throughout the 3D matrix for potential drug screening applications.

Recent advances in micro- and nanoscale (i.e. micropatterning, microfluidics) technologies have enabled the development of innovative platforms to study cancer cell migration within well-defined 3D microenvironments. Despite significant progress, most of the previously developed platforms have relied on simplified models to study the effects of a limited number of microenvironmental cues (i.e., matrix elasticity) on cancer metastasis. For instance, only a few studies have incorporated stromal cells (i.e. macrophages, FBs) within their model to recapitulate a physiologically relevant tumor microenvironment.

The breast tumor microenvironment is a complex milieu consisting of numerous cells types including fibroblasts and immune cells, packed in extracellular matrix (ECM), along with a dense network of capillaries. While previous research has demonstrated that the crosstalk between the cancer cells and their surrounding microenvironment significantly influences their metastatic potential, the success of therapeutic approaches to suppress breast tumor progression has been insufficient. A critical challenge in efficient translation of therapeutic strategies to clinical practice is the lack of physiologically relevant tumor models to study metastatic dispersion of cancer cells in response to microenvironmental stimuli within well-controlled experimental conditions.

Accordingly, due to the complexities associated with the native tumor stroma, there is an unmet need to develop physiologically relevant model in vitro microenvironments, in order to explore the metastatic behavior of cancer cells in response to a wide range of biophysical and biochemical stimuli.

BRIEF SUMMARY

To address these challenges, we developed an innovative approach using microscale technologies and hydrogel based biomaterials to develop a three dimensional (3D) in vivo like breast tumor microenvironment on a microfluidic chip. Specifically, we used microengineering technology, hydrogel-based biomaterials, and co-culture of key cell types within the tumor stroma to develop an in vivo like 3D vascularized human breast tumor model microenvironment. Hydrogels are excellent scaffolding materials because of their 3D architecture resembling the native in vivo microenvironment, homogenous cellular distribution, excellent diffusion properties and tunable mechanical characteristics. To date, hydrogels have been extensively used to study vascularization/angiogenesis, cell invasion and tissue morphogenesis. Integration of microscale (i.e. microfluidics) technology and biology not only offers high throughput systems but also enables tight control of the cellular microenvironment by varying cell-cell, cell-substrate, and cell-soluble factors interactions. Using microfabrication techniques, it is possible to create precisely defined features and organized cellular constructs to address the limitations of the conventional 2D assays and 3D macroscale hydrogel constructs.

Surrounding stroma embedded with inflammatory and immune cell (i.e. FBs, macrophages) plays a crucial role in cancer progression. In particular, FBs have been shown to exhibit activated phenotype with significantly higher proliferation and ECM deposition (collagen I) within the tumor stroma. Moreover, there have been studies demonstrating the FBs and inflammatory cells are principal source of host-derived VEGF secretion, which result in increased vascular permeability and ultimately enhanced angiogenesis within the tumor microenvironment. Therefore, co-culture of FBs, macrophages and ECs along with metastatic breast cancer cells provides a promising path to assess the influence of other cells types on cancer migration through the surrounding stroma. The unique features of the disclosed devices and methods bridge the gap between conventional 2D/3D assays and animal models to recapitulate the complexities associated within the native tumor stroma.

Accordingly, in a first aspect, the disclosure encompasses a microfluidic device that includes (a) a surface defining one or more microfluidic channels; (b) a first three dimensional scaffold comprising one or more cancer cells that is spatially separated from the one or more microfluidic channels; and (c) a second three dimensional scaffold, at least a portion of which is interposed between the one or more microfluidic channels and the first three dimensional scaffold. The second three dimensional scaffold is in fluid communication with both the first three dimensional scaffold and the one or more microfluidic channels.

In some embodiments, the cancer cells are breast cancer cells. In some embodiments, the one or more cancer cells are metastatic or tumorigenic cancer cells. In some such embodiments, the one or more metastatic or tumorigenic cancer cells are metastatic or tumorigenic breast cancer cells.

In some embodiments, the second three dimensional scaffold comprises one or more stromal cells. In some such embodiments, the one or more stromal cells are fibroblasts. In some embodiments, the second three dimensional scaffold comprises one or more macrophages.

In some embodiments, one or more of the microfluidic channels include one or more endothelial cells. In some such embodiments the endothelial cells form a monolayer in the on the surface of the microfluidic channel.

In some embodiments, the first three dimensional scaffold, the second three dimensional scaffold, or both comprise a gel matrix. In some such embodiments, the gel matrix comprises one or more of the group consisting of collagen, fibronectin, hyaluronan, a hydrogel, a peptide gel, and a gel-like protein, or interpenetrating network hydrogels. In some such embodiments, the gel matrix comprises a collagen hydrogel.

In some embodiments, the surface comprises a polymer. In some such embodiments, the polymer is polydimethylsiloxane (PDMS) or poly(methylmethacrylate) (PMMA).

In some embodiments, the surface extends beyond the one or more microfluidic channels, and the extended surface underlies both the first and second three dimensional scaffolds.

In some embodiments, at least a portion of the surface is patterned. In some embodiments, the surface further includes microposts separating the one or more microfluidic channels from the second three dimensional scaffold.

In some embodiments, the device further includes one of more inlets for adding the first three dimensional scaffold, the second three dimensional scaffold, or both to the microfluidic device.

In some embodiments, the microfluidic channels include one or more fluidic inlets suitable for introducing a test agent into the microfluidic device.

In some embodiments two microfluidic channels are disposed along two opposite sides of the second three dimensional matrix.

In some embodiments, the one or more cancer cells are obtained directly from a cancer patient in need of treatment.

In a second aspect, the disclosure encompasses a method of assaying a test agent for anti-cancer activity. The method includes the steps of (a) providing a microfluidic device as described above; (2) introducing the test agent to the microfluidic device through the one or more fluidic inlets; and (3) observing the cancer cells within the microfluidic device to determine the effect of the test agent.

In some embodiments, the cancer cells are obtained directly from a patient in need of treatment.

In a third aspect, the disclosure encompasses a method of studying cancer or related cells. The method includes the steps of (1) providing a microfluidic device as described above; and (2) observing one or more of the cancer cells, stromal cells, or epithelial cells within the microfluidic device.

In some embodiments, the method further includes the steps of altering one or more microenvironments within the microfluidic device, and determining the effect of the alteration on the one or more cells.

In a fourth aspect, the disclosure encompasses a microfluidic device that includes a surface defining one or more microfluidic channels; a first three dimensional scaffold comprising one or more cancer cells that is spatially separated from the one or more microfluidic channels; a second three dimensional scaffold, at least a portion of which is contacting and in fluid communication with the first three dimensional scaffold, and that is spatially separated from the one or more microfluidic channels; and a third three dimensional scaffold, at least a portion of which is contacting and in fluid communication with the one or more microfluidic channels and the second three dimensional scaffold.

In some embodiments, the one or more cancer cells are metastatic or tumorigenic cancer cells.

In some embodiments, the one or more cancer cells are breast cancer cells.

In some embodiments, the second three dimensional scaffold comprises one or more stromal cells.

In some embodiments, the one or more stromal cells are fibroblasts.

In some embodiments, the second three dimensional scaffold comprises one or more macrophages.

In some embodiments, the third three dimensional scaffold comprises one or more endothelial cells.

In some embodiments, one or more of the microfluidic channels comprises one or more growth factors.

In some embodiments, at least one of the first three dimensional scaffold, the second three dimensional scaffold, and the third three dimensional scaffold comprise a gel matrix.

In some embodiments, the gel matrix comprises one or more of the group consisting of collagen, fibronectin, fibrinogen, hyaluronan, a hydrogel, a peptide gel, a gel-like protein or interpenetrating network hydrogels.

In some embodiments, the gel matrix comprises a collagen hydrogel.

In some embodiments, the surface extends beyond the one or more microfluidic channels defined thereby, and wherein the extended surface underlies both the first, second, and third three dimensional scaffolds.

In some embodiments, the surface further comprises microposts separating at least one of the first three dimensional scaffold, the second three dimensional scaffold, the third three dimensional scaffold, and the one or more microfluidic channels along the portion that contacts. In some embodiments, the device further comprises one or more inlets for adding at least one of the first three dimensional scaffold, the second three dimensional scaffold, and the third three dimensional scaffold to the microfluidic device.

In some embodiments, the one or more of the microfluidic channels comprises one or more fluidic inlets suitable for introducing a test agent into the microfluidic device.

In some embodiments, the one or more microfluidic channels comprises a first microfluidic channel on a first side of the third three dimensional scaffold and a second microfluidic channel on an opposite second side of the third three dimensional scaffold.

In some embodiments, the one or more cancer cells are obtained directly from a cancer patient in need of treatment. The fibroblasts may be obtained directly from a cancer patient in need of treatment. The one or more macrophages may also be obtained directly from a cancer patient in need of treatment. The one or more endothelial cells may also be obtained directly from a cancer patient in need of treatment.

In a fifth aspect, the disclosure encompasses a method of assaying a test agent for anti-cancer activity in which the test agent is introduced to the microfluidic device through the one or more fluidic inlets; and the cancer cells are observed within the microfluidic device to determine the effect of the test agent. The cancer cells may be obtained directly from a patient in need of treatment or commercially available cells lines.

In a sixth aspect, the disclosure encompasses a method of studying cancer or related cells in which one or more of the cancer cells or related cells are observed within the microfluidic device. The method may further comprise the steps of altering one or more microenvironments within the microfluidic device and determining the effect of the alteration on the one or more cancer cells or related cells.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will be better understood and features, aspects and advantages other than those set forth above will become apparent when consideration is given to the following detailed description thereof. Such detailed description makes reference to the following drawings, wherein:

FIG. 16 is a table listing quantified values of the secreted cytokines from FIG. 15, B.

Figure 1:
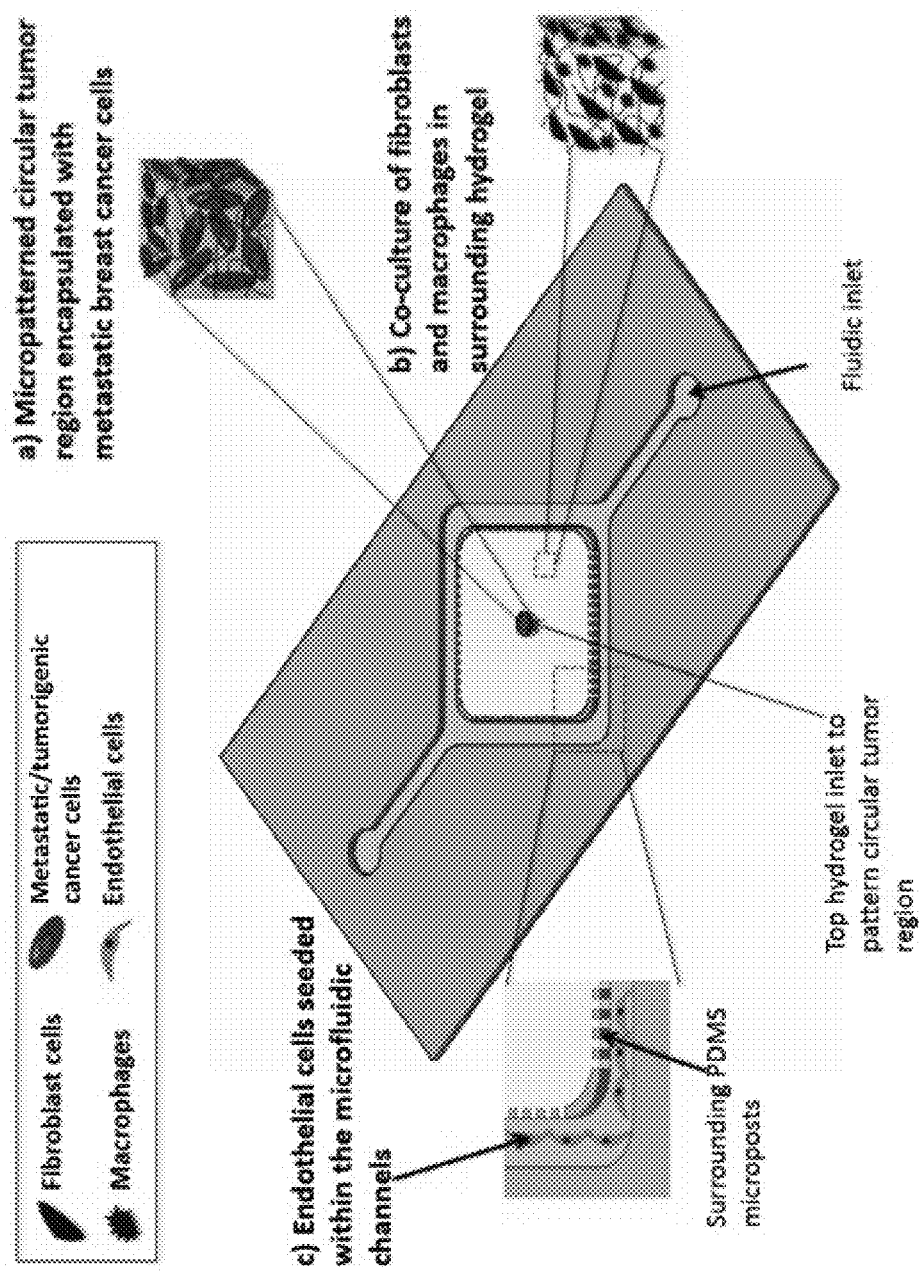
FIG. 1 is a schematic top view of a first exemplary microfluidic device.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, non-limiting exemplary methods and materials are described herein.

A major challenge in treatment of metastatic disease is the lack of suitable tumor models to test the efficacy of various therapeutic compounds in a high throughput and combinatorial fashion. Unfortunately, there are notable limitations associated with the previously reported tumor models. Genetically modified animal models (i.e. mouse) have been crucially important to define the molecular basis of disease progression; however, there are certain difficulties in distinguishing the effects of various microenvironmental cues on disease progression. Furthermore, in many scenarios, the main components of these models are mouse origin, while only the tumor cells are of human origin.

On the other hand, a large body of previously reported in vitro assays have used two dimensional (2D) platforms under mono-culture conditions. Other limitation of in vitro models include the use of immortalized or commercially available cell lines rather than patient derived primary cells. The development of preclinical in vivo like tumor models using clinical samples is particularly appealing in personalized medicine, as there is a significant heterogeneity within the population of cancer cells derived from patients.

To address these challenges, we disclose herein using microengineering technology, hydrogels, and patient specific primary cells to develop a three dimensional (3D) breast tumor microenvironment on a chip. Our platform facilitates clinically translatable techniques to study cancer cell line as well as patient specific tumor metastasis. In addition, the proposed platform can be independently used to assess the effects of various therapeutic compounds on cancer cells metastasis in a combinatorial and high throughput manner. We envision that the proposed technology will have an enormous impact on the lives of numerous patients suffering from breast cancer, through the development of personalized therapeutic regimens.

Accordingly, we disclose herein using hydrogel-based biomaterials and microfabrication/microfluidics technologies to precisely engineer a 3D biomimetic human breast tumor microenvironment on chip to study the malignant behavior of cancer cells within three specific stages including: a) Dissemination from the primary tumor region, b) Migration through the surrounding matrix and c) Intravasation.

There are four major innovative aspects disclosed herein. First, the disclosed approach utilizes an integrative strategy to merge microscale technology and hydrogels to develop a 3D tumor model. While, there has been extensive amount of effort toward the development of in vitro assays to study the malignancy of breast cancer cells, most of the previously reported platforms have been limited in terms of simplified culture conditions, such as using two dimensional (2D) surfaces or static growth environment. A major challenge in using such assays is the interpretation of the outcome, as these assays significantly deviate from the native microenvironment cancer cells experience. Herein, we disclose using hydrogels, as excellent scaffolding materials, to provide a 3D microenvironment to support cellular function. Furthermore, through the use of microengineering technology, we can precisely control the location of tumor construct and the surrounding stroma. For example, using the disclosed devices, we can localize cancer cells within a well-defined 3D hydrogel constructs and precisely engineer a neoplastic lesion, which is primarily isolated from the surrounding microenvironment. The microfluidic platform will provide a perfusable system where it would be possible to accurately control the culture condition and the distribution of the soluble factors throughout the hydrogel construct in a real time fashion.

Second, the proposed platform has enormous potential to be incorporated with patient specific primary cells and fresh tumor biopsies rather than just relying on the use of immortalized and commercially available cell lines. Our strategy is particularly appealing, since the use of patient derived primary cell provides a strategy toward more personalized, more effective and less toxic treatment to breast cancer patients. In particular, we can selectively use a single microengineered chip to study the drug responsiveness of cancer patients in combinatorial therapeutic regimens. Furthermore, the proposed technology provides a solid foundation to overcome the challenges associated in cancer therapy due to heterogeneous population of tumor cells derived from individual patients.

Third, the majority of the previously reported in vitro assays have been founded on the use of single cell types (i.e.

metastatic cancer cells). However it is becoming well recognized that the surrounding stroma embedded with fibroblasts and inflammatory/immune cell plays a crucial role in cancer progression. Particularly, numerous studies have demonstrated that the cross-talk through paracrine signaling between cancer cells and the stromal cells, such as fibroblasts, significantly influence their malignancy. As a result, there is an increasing interest toward exploring novel therapeutic compounds targeting the tumor microenvironment. Unfortunately previous studies have not incorporated the crucial components of the native tumor microenvironment in their model system.

In the disclosed systems, we have modeled these complexities while developing a physiologically relevant tumor microenvironment to study metastatic cells dissemination and migration of the cancer cells.

In some of the exemplary embodiments disclosed herein, fibroblast cells and macrophages are incorporated within the model tumor microenvironment. However, a central feature of our approach is the modularity of the proposed platforms in terms of: a) flexibility in the selection of appropriate biomaterials with variable stiffness and porosity to construct the 3D tumor microenvironment, and b) inclusion of other cell types such as immune/inflammatory cells, endothelial cells. Overall, with the disclosed design, we will be able to tune the complexity of the proposed platform toward the targeted study.

Fourth, the disclosed microengineered platform allows recovering samples from different locations of the chip, in order to assess the correlation between the genetic heterogeneity of cancer cells to their migration profile within the 3D hydrogel constructs.

This disclosure is directed to a microfluidic device that includes one or more microfluidic channels and two different three dimensional scaffolds, each three dimensional scaffold containing, e.g., a 3D gel matrix contained within a chamber of the microfluidic device. The first three dimensional scaffold includes encapsulated cancer cells, while the second three dimensional scaffold may include encapsulated stromal cells, such as fibroblast cells, and may further include macrophages. At least a portion of the second three dimensional scaffold is interposed between the first three dimensional scaffold and the one or more one or more microfluidic channels. The interposed second three dimensional scaffold is in fluid communication with (i.e., fluidically coupled with) both the microfluidic channels and the first three dimensional scaffold.

A microfluidic channel, as the terms is used herein, typically has a channel width perpendicular to a longitudinal axis of the channel (i.e., a path along which fluid flows during ordinary operation) that is about 1 mm or smaller. In general, the channel width depends on the particular application. For example, for creating cellular monolayers, channel widths may range, in certain non-limiting embodiments, from about 200 µm to about 1200 µm, from about 300 µm to about 1100 µm, from about 400 µm to about 1000 µm, or from about 400 µm to about 600 µm. The cross-sections of the microchannels (perpendicular to the respective longitudinal axes) may be rectangular, round, or have any other shape, and may (but need not) vary in size or shape along the longitudinal axes.

The three dimensional scaffolds allow fluid flow and cell migration through the scaffolds, between the scaffolds, and between the scaffolds and the microfluidic channels (i.e., the three components are in "fluid communication" with each other). Thus, in embodiments having two different microfluidic channels on opposite sides of the microfluidic device, by establishing fluid flows in the two microfluidic channels that differ in their respective pressures and/or the concentrations of one or more fluid constituents (e.g., a pharmaceutical compound, biochemical factor, etc.), a pressure and/or concentration gradient may be established across the 3D scaffolds. In certain embodiments, the two microfluidic channels may have separate or common inlets, but merge downstream the 3D scaffold to share a common outlet. As a result, the pressures in the two channels are substantially equalized, such that a pressure gradient across the 3D scaffold is avoided, as is desired for some applications. At the same time, a controlled concentration gradient can be established across the 3D scaffolds by injecting fluids of different compositions at the inlets upstream of the scaffolds.

In some embodiments, the microfluidic device may have non-uniformly treated and/or patterned interior surfaces. The interior surface of a microfluidic device includes the walls of the microfluidic channels, as well as the walls of any other hollow spaces formed in the polymer (or other solid) structure defining the device, such as, e.g., the walls of the gel-holding chamber. Surface treatment and/or patterning include chemical and/or topographical surface modifications. Chemical modifications, in turn, include treatments and/or coatings with inorganic substances as well as with organic substances (such as, e.g., antibodies or proteins). Non-uniform surface treatment implies that one or more portions of, but less than the entire, surface is treated, or that different portions are treated in different ways.

Patterning implies repetitive (although not necessarily perfectly regular) surface modifications. For example, in some embodiments, one or more microchannel walls may feature chemically (including, e.g., biologically) treated islands, or non-treated islands defined by an otherwise treated surface area. Further, in some embodiments, certain interior surfaces are topographically structured, e.g., with microposts. Microposts disposed at the top and bottom surfaces of a gel-containing chamber may serve to hold the gel in place. Further, microposts and other topographical structures may be used to influence the interactions of cells with the walls. Microposts at oblique angles to the surface may, for instance, be used to adjust the apparent "softness" of the walls for purposes of cell-wall interactions.

The microfluidic devices as described herein may be used for culturing and observing cells in a controlled microenvironment. Applications include, for example, cell migration, proliferation, and differentiation studies (e.g., angiogenesis investigation), and the analysis of biophysical and biochemical factor influence on cell function (including, e.g., drug safety and efficacy testing). Commercial applications of the devices described herein include, but are not limited to, evaluating cancer therapies, quantifying cancer cell migration, testing pharmaceuticals, and individualizing an anti-cancer treatment to a specific patient's tumor type.

The three dimensional scaffolds may include or consist essentially of a gel matrix, which may comprise a gel or gel-like material such as, e.g., collagen, fibronectin, hyaluronan, a hydrogel (such as, e.g., polyethylene glycol hydrogel), a peptide gel, or gel-like proteins or protein mixtures secreted by animal cells (e.g., Matrigel™) as well as interpenetrating network hydrogels. Non-limiting examples of polymers that can be used to construct the disclosed microfluidic devices include polystyrene, polydimethylsiloxane, polycarbonate, poly(methyl methacrylate), cyclic olefin copolymer, polyethylene, polyethylene terephthalate, polyurethane, polycaprolactone, polylactic acid, polyglycolic acid, or poly(lactic-co-glycolic acid). In some embodiments, different types of polymers are used for different components or portions of the polymer structure. The polymer structure may be substantially optically transparent (e.g., have a transmission in the visible range of more than 70%, preferably more than 90%, and more preferably more than 95%).

In certain embodiments, the upper and/or lower surface of the chamber that contains the three dimensional scaffolds may features surface modifications, which may serve to hold the scaffolds in place. For example, the surface(s) may be modified with microposts disposed thereon. Further, in some embodiments, the surface(s) of one or both microchannels, or one or more surface portions, are patterned (e.g., chemically or topographically). The surface patterning may be non-uniform.

In one exemplary embodiment, the present disclosure provides a unique microfluidic in vitro model comprising of three distinct, but interconnected layers. This enabled spatial organization and compartmentalization of tumor, stroma and endothelial entities. Geometry and design enabled side-by-side arrangement of the tumor and stromal components in the 3D matrix, and it also may incorporate diffusive barriers for transport of nutrients and growth factors thereby enabling bi-directional crosstalks between the different layers. Compared to other in vitro models for invasion and intravasation, some aspects of the model present various advantages in developing comprehensive assays, such aspects may include: (i) a well-formed solid tumor surrounded by stroma allows modeling of the cancer invasion from the primary tumor to a stromal region in response to secreted biomolecules. This further allows one to quantify the number as well as the morphology of the invading cancer cells. (ii) Having separated but interconnected compartments for tumor and endothelial cells enables studying both the cancer cell behavior and vasculogenesis simultaneously. One can observe growth and maturation of vascular networks and quantify the morphological characteristics of the endothelium in response to cancer cell signaling. The architecture of the model may also enable permeability studies on mature microvessels and help to elucidate the changes in permeability of the formed vasculature due to tumor-endothelial interactions. (iii) Both cancer and endothelial cells are embedded in 3D matrices, facilitating cell-cell and cell-ECM interactions mimicking the complex tumor microenvironment. (iv) Another advantage is the capability to obtain the dynamics of high-tumor-endothelial interactions during cancer cell invasion and intravasation in a real time fashion by tracking at a single cell level during invasion and intravasation.

The invention will be more fully understood upon consideration of the following non-limiting Example.

EXAMPLES

Example 1

An Exemplary Microfluidic Device

In this example, we describe a non-limiting exemplary embodiment of a microfluidic device according to the disclosed invention.

FIG. 1 shows the features of the exemplary microfluidic device. As shown in FIG. 1, the microfluidic device includes two separate regions of hydrogel constructs, one for the circular tumor construct (neoplastic lesion) encapsulated with metastatic breast cancer cells ((a); center circle), and the second one resembling the surrounding 3D ECM stroma for encapsulation of FBs and macrophages ((b); rectangle surrounding center circle). Two parallel microfluidic channels seeded with ECs are interconnected with the surrounding ECM hydrogel ((c), adjacent to the two long edges of rectangle of (b)). In particular, the microfluidic channels will be used for seeding of ECs resembling the vascular network ((c)). In addition, the microfluidic channels will be used to introduce anticancer drugs for testing.

Microfluidic Device

The preliminary design of the exemplary microfluidic device can be performed using AutoCAD, based on the following dimensions:

| Design designation | Channel length/width/height | Surrounding hydrogel dimensions | Micropost Spacing |
|---|---|---|---|
| A | 8 mm/500 μm/150 μm | 4 mm × 4 mm | 100 μm |
| B | 6 mm/500 μm/150 μm | 3 mm × 3 mm | 100 μm |
| C | 5 mm/500 μm/150 μm | 2.5 mm × 2.5 mm | 100 μm |
| D | 6 mm/500 μm/150 μm | 3 mm × 3 mm | 150 μm |

The exemplary microfluidic devices may be fabricated in polydimethylsiloxane (PDMS) using replica molding technique. For drug testing applications, other hydrophilic materials, such as functionalized Poly(methylmethacrylate) (PMMA), may be used instead of PDMS to fabricate the device. However, the fabrication process would be similar to that used for PDMS.

Briefly, transparency masks, design by AutoCAD (minimum features of 20 μm), are used for SU-8 photolithography to create the silicon wafer master. PDMS and the curing agent are mixed in 10:1 (base:curing) ratio, and the solution is poured over the silicon wafer master, degassed and put in an 80° C. oven for 2 h. Upon polymerization, PDMS wafer is peeled off from the silicon wafer master, and each microfluidic device is cut.

The inlet and outlets may be cored down to the microfluidic channels using a standard 1 mm diameter punch. Prior to cell culture experiments, the microfluidic device is sterilized in 120° C. for 20 min in a wet cycle, followed by a dry cycle at 120° C. for 35 min. The PDMS surfaces of the microfluidic device is rendered hydrophilic by using air plasma to enhance hydrogel loading within the device, according to previously published procedures.

Finally, the PDMS devices are each bonded to a glass cover slip through oxygen plasma treatment. The edges of the hydrogel injection channels may be tapered in order to reduce bubble formation.

Cell Encapsulation and Hydrogel Injection

Collagen type I (or alternative) hydrogel may be used for cellular encapsulation and construction of the 3D microenvironment. The lyophilized protein is dissolved in 0.02 N acetic acid to obtain a collagen solution with 1-4 mg/ml concentration. Breast carcinoma (i.e. MDA-MB-231) expressing mCherry fluorescent protein, human umbilical vein endothelial cells (HUVECs) expressing green fluorescence protein, human mammary FBs and human macrophage cell line U937 may be used in this work.

FBs and macrophages may be encapsulated in a collagen hydrogel (surrounding stroma, FIG. 1), with the densities of $3.2 \times 10^6$ and $0.8 \times 10^6$ cells/ml (ratio 4:1), respectively. The surrounding hydrogel can be injected from the inlets located at the top. Upon gel injection, the device is placed inside the humidified incubator for 30 min at 37° C., in a 5% $CO_2$ atmosphere, to polymerize the hydrogel construct.

Cancer cells may be encapsulated in collagen hydrogel prepolymer solution with the density of $0.5 \times 10^6$ cells/ml of hydrogel. A punch is used to core the center of the device creating a circular indentation in the stroma. The cell encapsulated hydrogel can be slowly injected from the top inlet of the microfluidic device, using image guided phase contrast microscopy and a microfluidic pump. (see FIG. 1).

Upon gel injection, the device is placed inside the humidified incubator for 30 min at 37° C., in a 5% $CO_2$ atmosphere, to polymerize the hydrogel construct. After hydrogel crosslinking, ECs may be seeded though the side channels with the density of $2 \times 10^6$/ml of media. As the stiffness of the soft breast tissue to stiff tumor is within the range of 0.2-4 kPa, the concentration of the collagen hydrogel may be varied (e.g., from 1-4 mg/ml), in order to tune the mechanical properties of the surrounding stroma.

Evaluation of the Platform Performance

The formation of EC monolayer through the microfluidic channels may be assessed through staining the GFP-expressing ECs with CD-31 and VE-cadherin cellular junction protein after 48 h of culture. Primary and secondary Alexa Fluor conjugated 595 secondary antibodies specific to human ECs (Abcam) may be used to for staining of CD-31 and VE-cadherin. Cell-cell junctions may be carefully visualized through high magnification (40x) fluorescence microscopy, and the fluorescence intensity of cellular junctions may be measured using NIH Image J software. These analyses will ensure successful seeding and coverage of the ECs within the inner layer of the microfluidic channels, thus resembling the vascularized networks.

To test the perfusion capacity of the microfluidic device and establishment of stable gradients of soluble factors through the surrounding hydrogel construct, Texas Red-conjugated Dextran (70 kDa, Invitrogen), diluted in EC basal media (concentration: 12.5 µg/mL) may be flowed through the channels at the rate of 1 mL/min. The gradient and the diffusion profile of the fluorescence molecules through the surrounding collagen hydrogel may be detected using real time fluorescence microscopy. The obtained fluorescent intensity data enables measurement of diffusive EC permeability (PD) according to the previously developed computational model: $PD = \beta \cdot D/\Delta C(dC/dx)$, where C is the dextran concentration (proportional to fluorescence intensity), $\Delta C$ the step drop in concentration across the monolayer (obtained from raw fluorescence data), $\beta$ is an area correction factor, $dC/dx$ is the slope of the concentration profile, and D is the dextran diffusion coefficient ($9 \times 10^{-11}$ $m^2/s$).

The permeability 48 h post seeding of ECs within the microfluidic channels may be measured for two time points (e.g., within 24 h and 48) within ten separate regions of the surrounding hydrogel in between the microfluidic channels and the circular tumor construct. Characterization of permeability may be validated through computational finite element modeling using COMSOL software.

Example 2

Production and Use of an Exemplary Microfluidic Device

In this proof of principal example, we demonstrate that a microfluidic device according to the disclosed invention is capable producing a well-defined tissue architecture, and that it enables high-contrast and real-time imaging for detailed invasion and intravasion studies.

Introduction

The development of our breast cancer invasion platform has given our laboratory the opportunity to investigate and provide insight to key aspects of the metastatic cascade and tumorigenesis. This study validates our model as breast cancer invasion and demonstrates that our platform is capable of producing a well-defined tissue architecture and enabling high-contrast real-time imaging for detailed invasion and intravasation studies.

Creating a Spatially Organized Cancer Invasion Platform

Figure 2A:
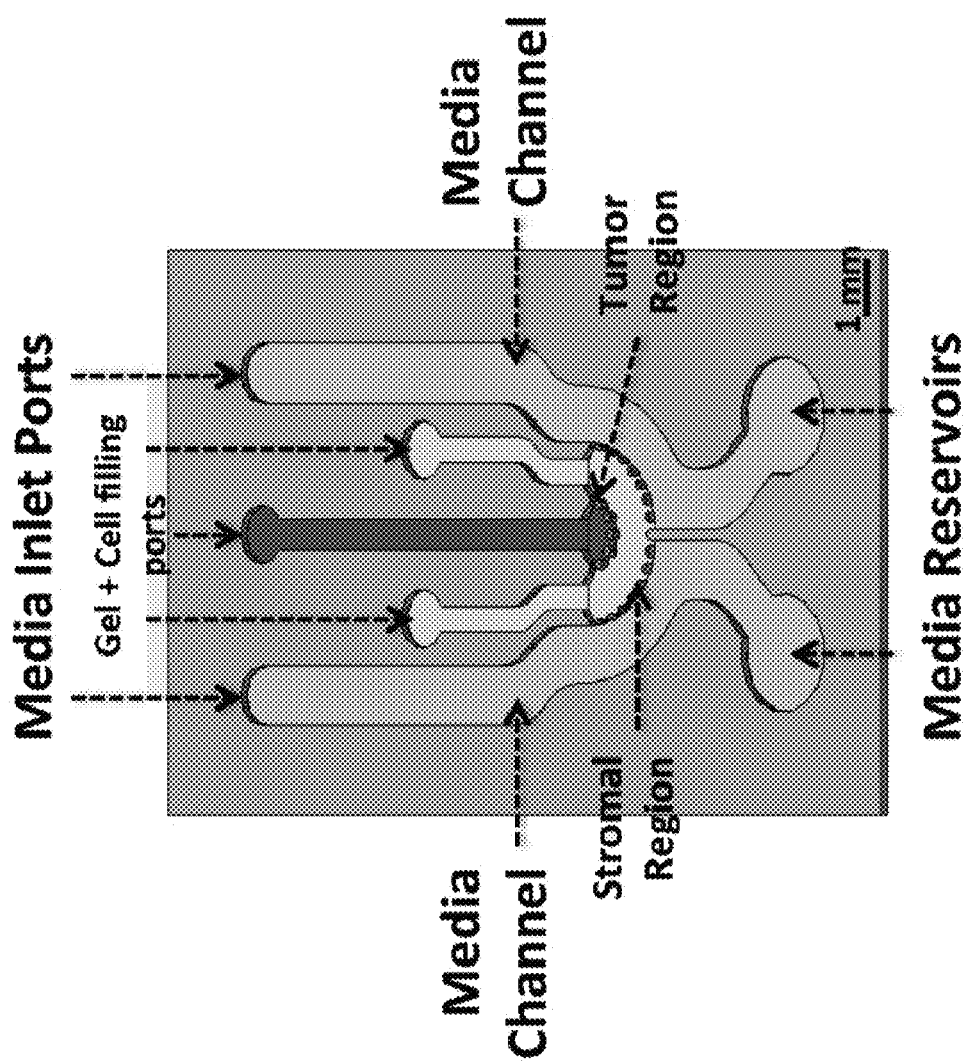
FIG. 2A is a schematic top view of a second exemplary microfluidic device.
Figure 2B:
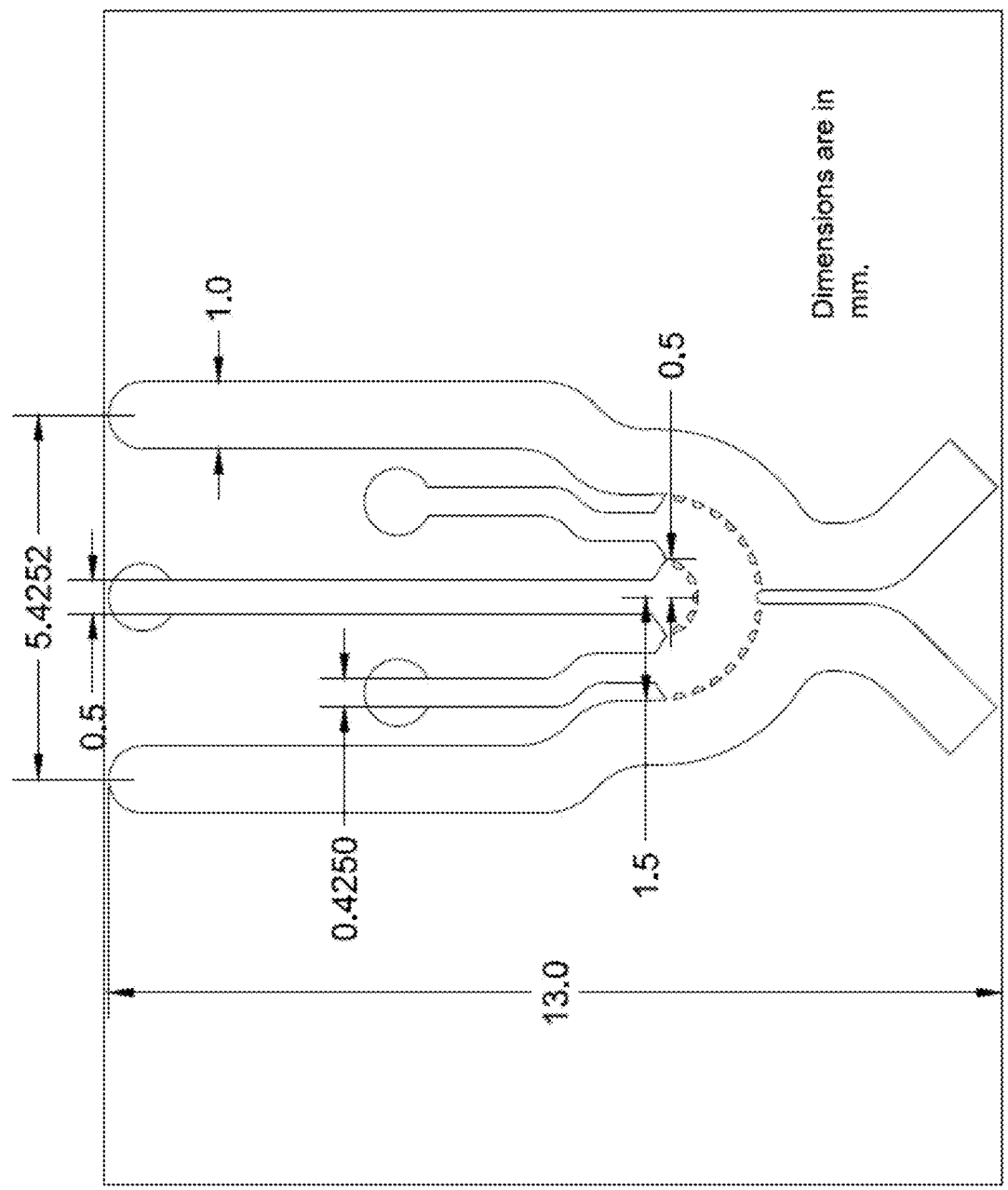
FIG. 2B is a schematic top view of one embodiments of the second exemplary microfluidic device, showing selected dimensions in millimeters (mm).
Figure 2C:
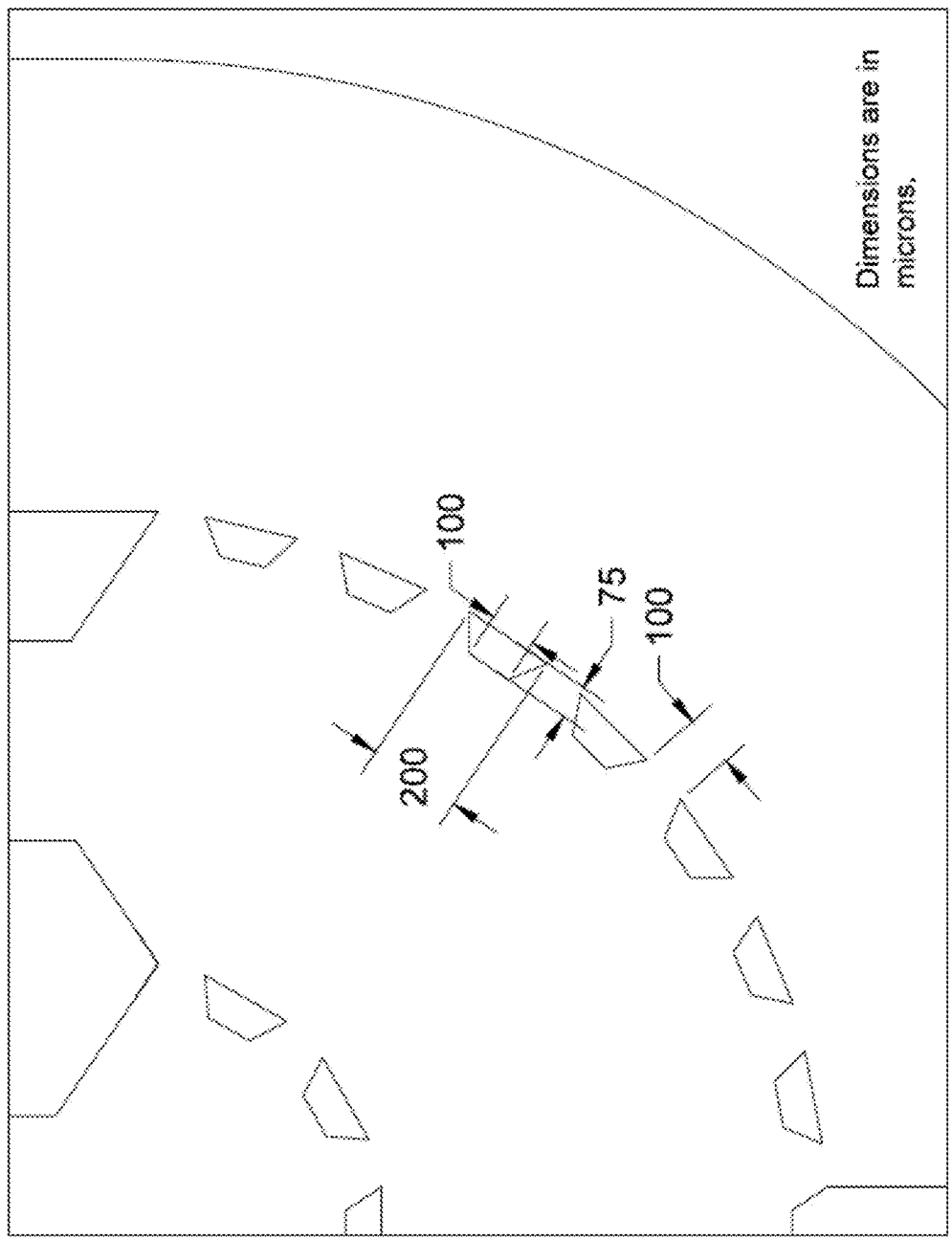
FIG. 2C is a schematic top view showing an enlarged section of FIG. 2B that includes the right half of the tumor and stromal regions and an associated section of the right media channel. Selected dimensions are shown in microns ($\mu$m).

First, we developed a CAD design that caters to the native breast tumor architecture (FIG. 2A). It consisted of two distinct region made up of two concentric semi-circles. The inner semi-circle represents the tumor region whereas the outer semi-circle represents the stromal region. We set the radius for the inner circle to be 0.5 mm and the radius for the outer circle was 1.5 mm. Additionally, there are two channels that flank the stromal region representing vascularized networks. The channels had a width of 1 mm and the final depth of the chambers was 200 microns. We used microposts comprising of trapezoids to confine the hydrogel matrix within the tumor and stromal regions based on the surface contact angle of collagen gel to PDMS (see FIGS. 2B and 2C).

Demonstrating Defined Regions within the Platform

Figure 3:
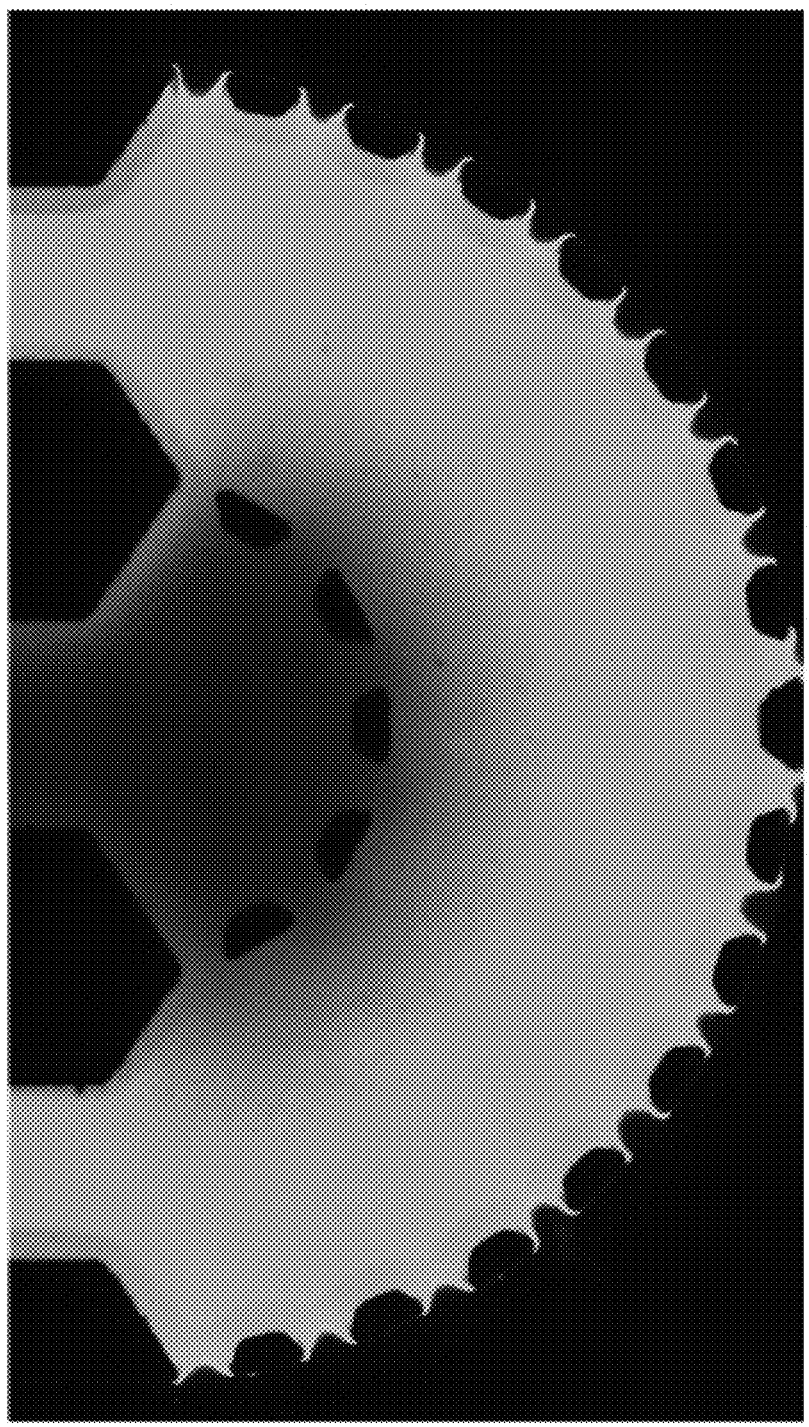
FIG. 3 is a photographic top view of a section of the second exemplary microfluidic device. A dark red dyed hydrogel defines the tumor regions and a green dyed hydrogel defines the stromal region.
Figure 4:
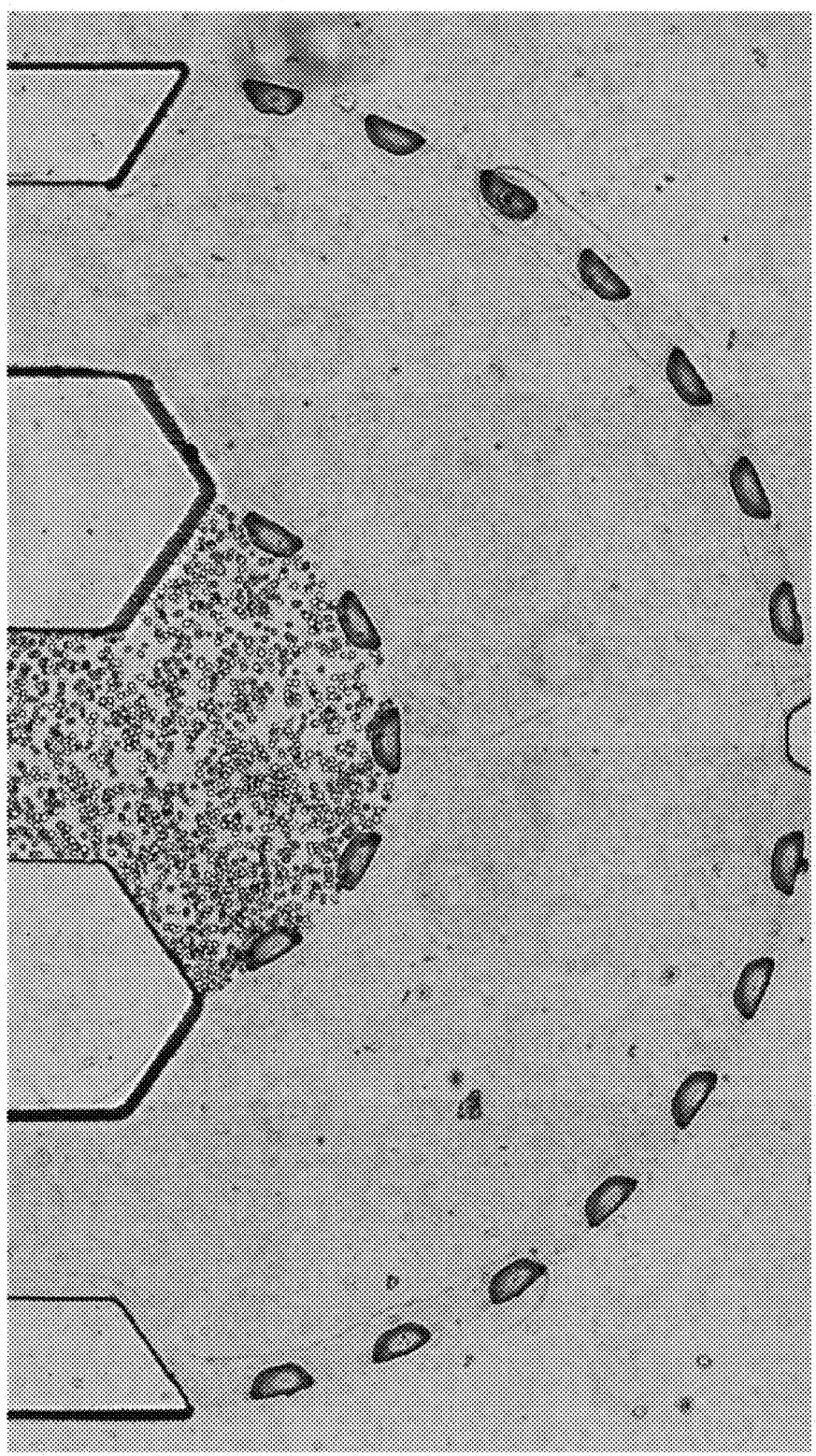
FIG. 4 is a photographic top view of a section of the second exemplary microfluidic device. Cancer cells are confined within the tumor region and cell-free collagen is confined within the stromal region.

We used a dyed hydrogel and injected it into the device to demonstrate the feasibility of creating defined regions within our platform (FIG. 3). By doing so, this implies that there can be two different hydrogels consisting of different cells, ECM proteins, stiffness, and growth factors arranged spatially. Furthermore, we validated this fact by injecting the tumor region with SUM-159 breast carcinoma cells encapsulated in collagen and subsequently injecting the stromal region with cell-free collagen (FIG. 4). In this regard, we demonstrated a clearly defined interface between the two regions of different composition representing the typical breast tumor architecture.

Characterizing Biomolecular Gradients

Figure 5:
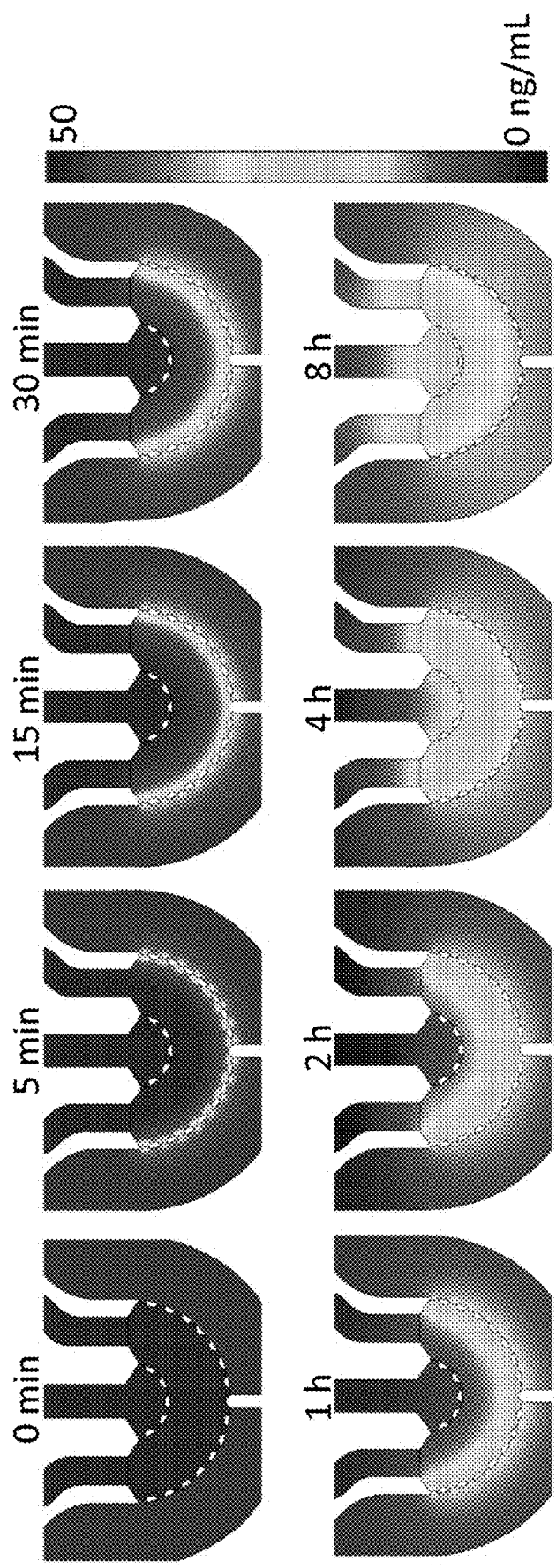
FIG. 5 is a software-generated model showing the development of a diffusive gradient over time in the second exemplary microfluidic device.

To show a steady chemogradient in our platform, we performed computational modeling to assess diffusion gradients using COMSOL Multiphysics software. The Stokes-Einstein equation was used to calculate diffusion coefficients for molecules of various molecular weights. For our device, we used 2 mg/mL of collagen type I as the encapsulating matrix. For the simulation, we used a 10 kDa molecule as a reference point and 50 ng/mL of the molecule was simulated diffusing into the tumor region. A stable gradient was established in the tumor region by 4 h (FIG. 5).

Chemoinvasion of Breast Cancer Cells

We encapsulated highly invasive SUM-159 breast cancer cells within our platform. Cells were encapsulated in a mixture of Collagen:Matrigel at a ratio of 1:1 (final collagen density is 1 mg/mL) and the solution was injected into the tumor region while cell-free collagen type I (2 mg/mL) was injected into the stromal region. In one platform, 50 ng/mL of epidermal growth factor (EGF) was injected to the side channels to stimulate chemoinvasion, while in a control platform, no EGF was injected. We observed the migration of the cells throughout the stromal region over the course of four days in both conditions.

Figure 6:
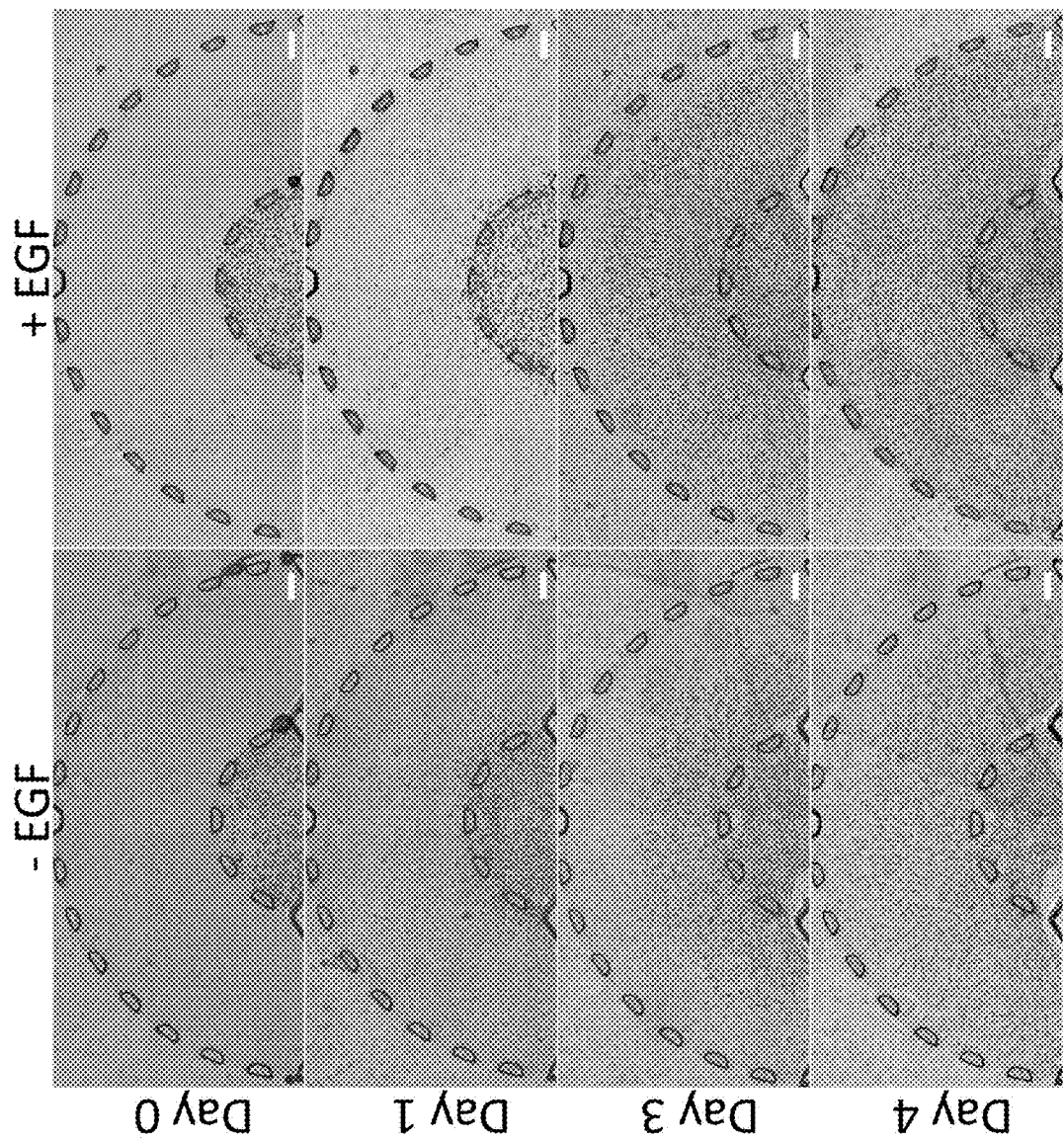
FIG. 6 is a series of photographs showing invasion of SUM-159 breast cancer cells over time within a section of the second exemplary microfluidic device. Chemoinvasion stimulated by epithelial growth factor (+EGF, right column) is compared to invasion of unstimulated control cells (−EGF, left column).
Figure 7:
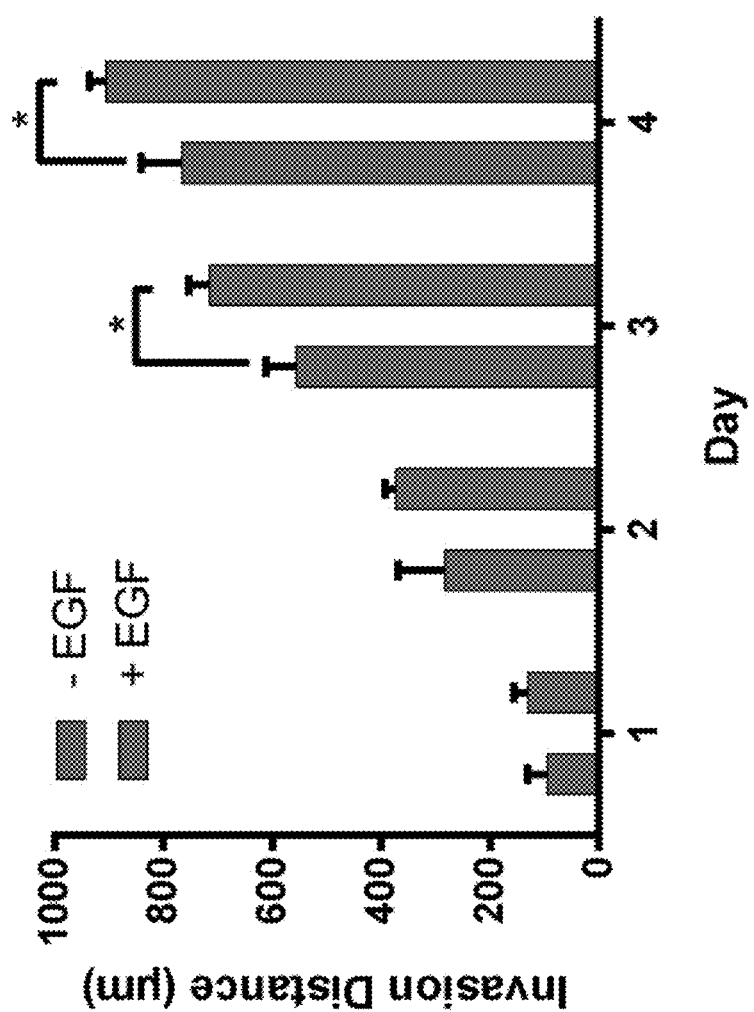
FIG. 7 is a graph showing invasion distance in $\mu$m as a function of days after SUM-159 breast cancer cell introduction within the second exemplary microfluidic device. Results are shown for both chemostimulated (red, +EGF) and unstimulated (blue, −EGF) trials.
Figure 8:
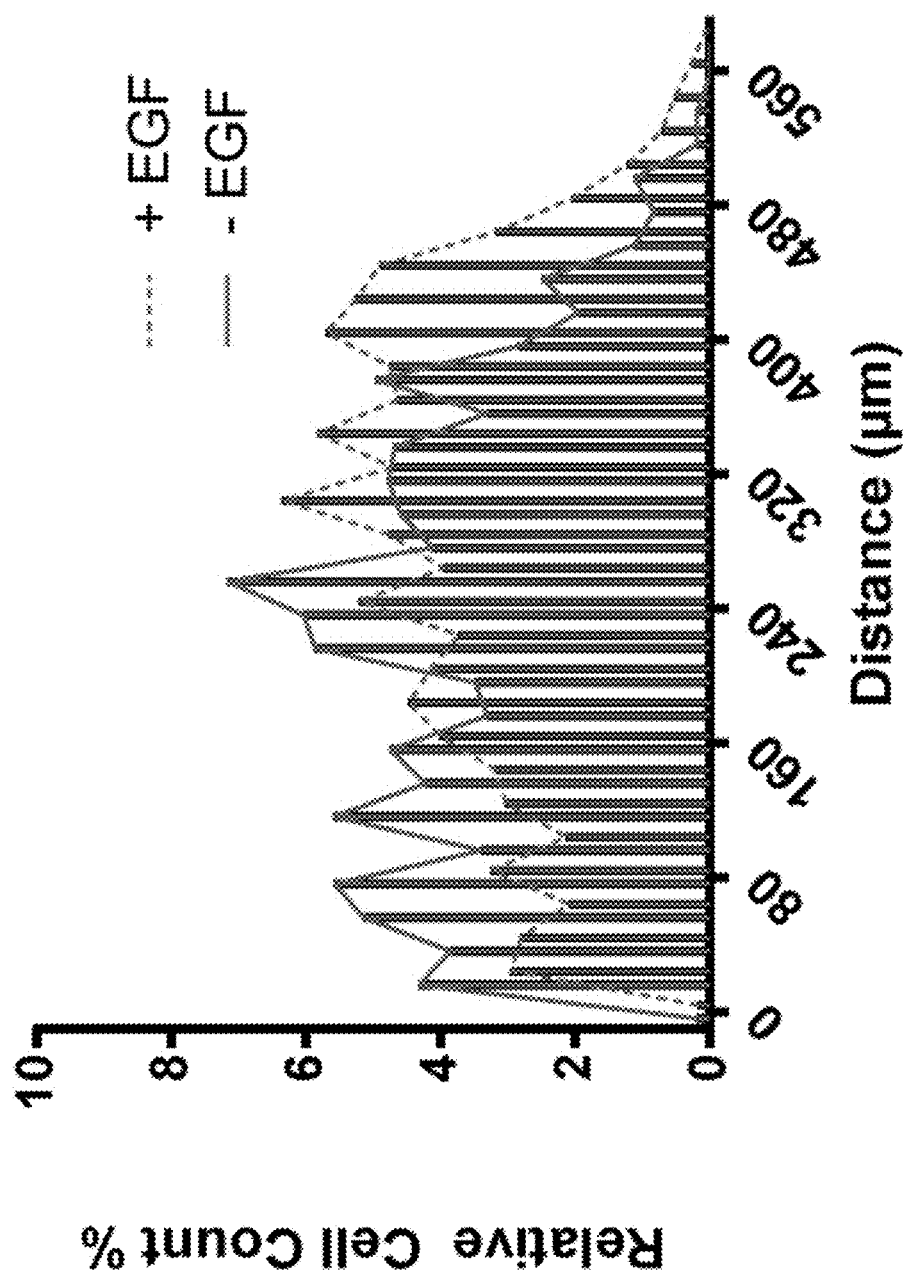
FIG. 8 is a graph showing relative cell count (as percent of total cells) as a function of migration distance four days after SUM-159 breast cancer cell introduction within the second exemplary microfluidic device. Results are shown for both chemostimulated (red, +EGF) and unstimulated (blue, −EGF) trials.
Figure 9:
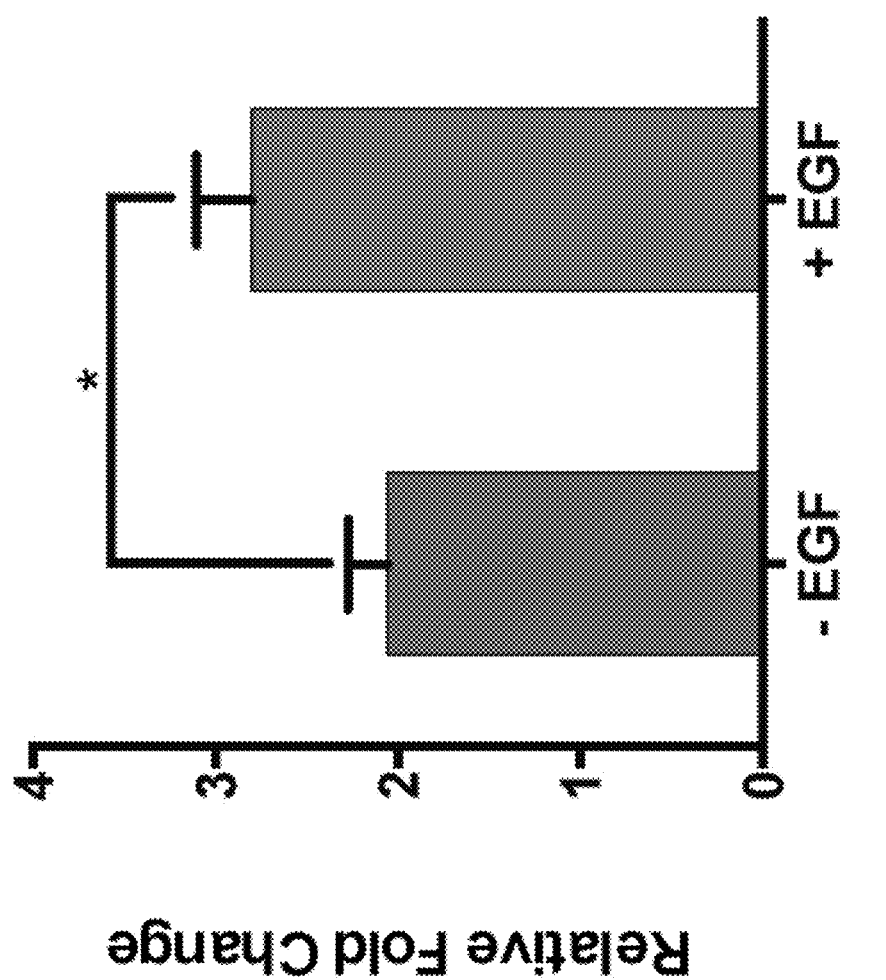
FIG. 9 is a graph showing fold change in SUM-159 breast cancer cell within the media channels of the second exemplary microfluidic device between three and four days after cell introduction within the second exemplary microfluidic device. Results are shown for both chemostimulated (red +EGF) and unstimulated (blue −EGF) trials.

As seen in FIG. 6, cells under both conditions began to invade the stromal region after one day. There was noticeable collagen deformation showing that the cells are actively sensing their biophysical environment and reacting to it. Additionally, cells within the tumor region demonstrated a round morphology while cells that invaded the stromal region demonstrated spindle-like morphology. By day 3, it was evident that cells stimulated by EGF invaded further (FIG. 7). Cells without EGF stimulation did invade as well but not by the same distance. By day 4 in the EGF stimulated group, more cells had migrated a greater distance (FIG. 8), and a higher number of cells were seen in the channels as compared to the –EGF control group (FIG. 9).

Example 3

Another Exemplary Microfluidic Device

In this example, we describe additional non-limiting exemplary embodiments of a microfluidic device according to the disclosed invention.

Introduction

In this newly developed platform, we created a novel microfluidic platform comprised of concentric three-layer cell-laden hydrogels, which allowed for simultaneous observation of vascular network maturation as well as breast cancer cell invasion and intravasation. We demonstrated that highly metastatic MDA-MB-231 disseminated from the primary tumor region and invaded into the adjacent stroma layer, where the presence of a vascular endothelial network in the third layer of the platform drastically increased cancer cell motility and invasion. Most importantly, by day 6 of culture, cancer cells could be visualized intravasating into the vasculature. Additionally, the presence of the invading cancer cells significantly reduced vessel diameter and increased permeability, consistent with previous in vivo studies. We also probed the conditioned medium from the invasion and intravasation assays using an antibody array and identified potential signaling candidates governing cancer migration in the presence of vascular networks. Taken together, our presented platform will enable unique insights into the cascade of critical biological events leading up to invasion and intravasation of tumor cells with significant potential for developing efficient cancer therapeutics.

To address the limitations of the previous works and gain a mechanistic insight on the biological interactions of tumor and endothelial cells, we aimed to develop a model with a well-formed 3D tumor and vascular network as well as a gradient of biomolecules to mimic in vivo tumor microenvironment.

Figure 10:
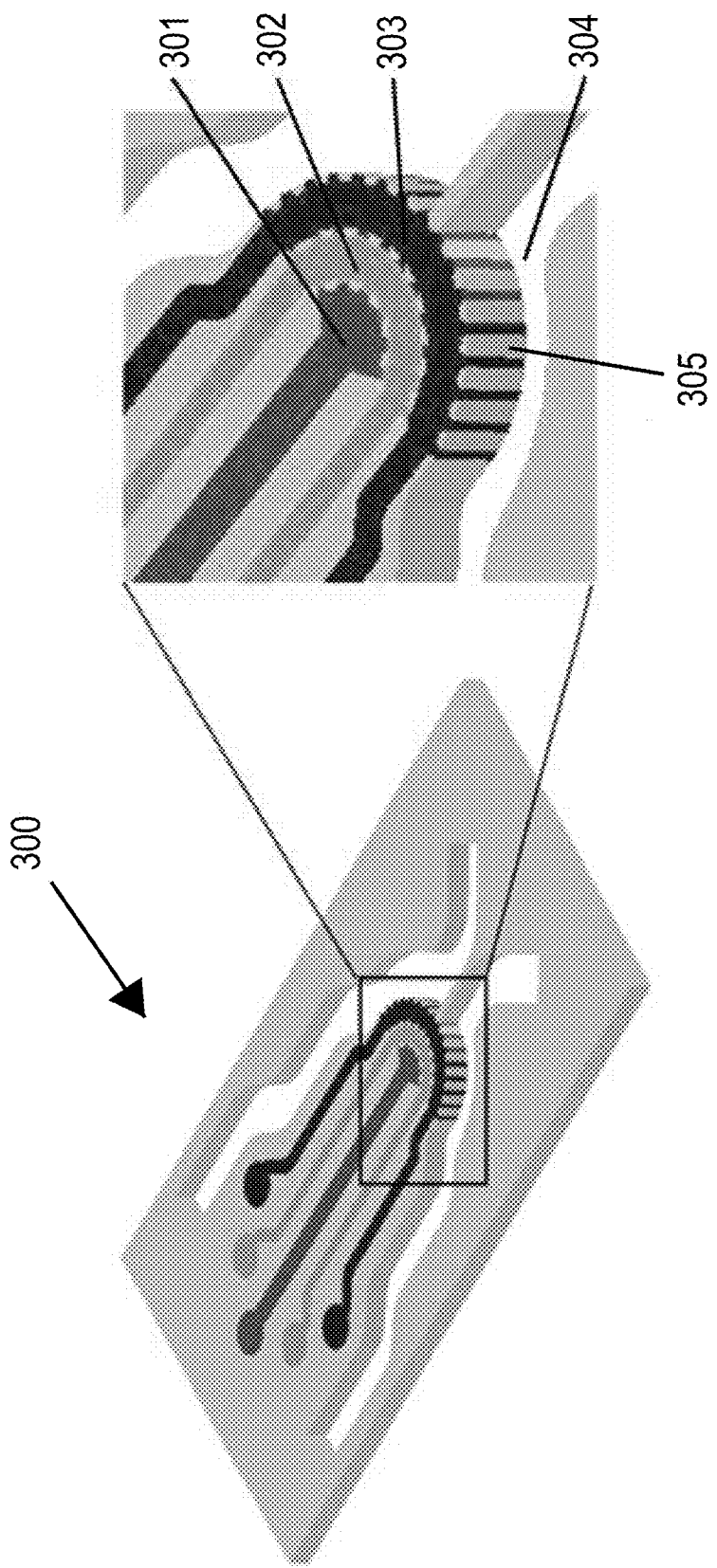
FIG. 10 is a schematic isometric view with a callout of a third exemplary microfluidic device.

As illustrated in FIG. 10, we have fabricated an integrated three-layer microfluidic device 300 consisting of a first scaffold 301, a second scaffold 302, and a third scaffold spatially organized side-by-side sequentially, while composed of physiologically relevant matrices and cell types to perform simultaneous molecular and cellular level studies on cancer cell invasion and intravasation on a single microfluidic device. The first scaffold 301, second scaffold 302, and third scaffold 303 may also be referred to as tumor, stroma and an endothelial layers or regions based on their compositions.

Our model allows introducing high-density cancer cell populations (20 million/ml) embedded in a collagen matrix, which better represents the 3D tumor mass inside the body. In addition, the endothelial region 303 contains a complex vascular microenvironment made up of endothelial cells (20 million/ml) forming a perfusable in vivo-like vessels. Another critical feature of our model is the geometry and design of the device 300. Having at least one microfluidic channel 304, also referred to as a media channel, surrounding endothelial region 303 and the tumor the tumor region 301 was critical for diffusion of nutrients to the cancer cells and cancer cells. In addition, the presence of middle stromal layer 302 allowed for visualizing and analyzing the cancer cells invading along with vascular development to assess cancer cells intravasation at a single cell level in a real time fashion.

Our findings demonstrated that the number of cancer cells invading stroma was increased in the presence of vascular network and cancer cells with elongated morphology. The structure of vascular network was also altered in the presence of tumor leading to formation of thinner and more permeable vessels. Most importantly, we utilized an angiogenesis antibody array and identified potential cytokine candidates, which may govern cancer migration in the presence of vascular networks. Overall, our study recapitulates dynamic interactions and signaling between cancer and formed vascular networks within a physiologically relevant model to unveil the biological mechanisms involved during invasion and intravasation. The proposed platform could be a potentially powerful technology to identify efficient therapeutic regimens to inhibit cancer metastasis.

Fabrication of the Microfluidic Platform

To fabricate the microfluidic devices 300, the required design was first made using CAD software. The design was then transferred to a transparent mask. Next, SU8-2075 (MicroChem) was spun to height of 200 μm onto a silicon wafer and afterwards, the wafer with the transparent mask beneath, was exposed to UV to form the primary mold. To make the surfaces of the silicon wafer hydrophilic, the wafers were treated with Methyltrichlorosilane (MTCS, Sigma-Aldrich). Then Polydimethylsiloxane (PDMS, Sylgard 184 Silicon Elastomer Kit, Dow Corning) was poured onto the wafer and baked for 1.5-2 hours at 80° C. The cast PDMS was peeled off the wafer to retrieve the PDMS molds. The molds were then cut using blades to separate individual devices, and inlet and outlet holes were made using biopsy punch. Next step was to bond the devices onto the glass slide to form the channels. To do so, first the devices and glass slides were cleaned with ethanol and nitrogen gas stream and subsequently treated with oxygen plasma (PDC-32G, Harrick Plasma) to make the surfaces hydrophilic. The devices were then bonded onto glass slide with the channel side facing down and placed in oven at 80° C. overnight to secure the bonds. To sterilize the devices, they were first put in the liquid autoclave followed by dry autoclave and then were placed in the oven at 80° C. to completely dry the devices.

Surfaces of the culture region in the device 300 must be treated in order to enhance attachment of the collagen gel. Therefore, poly-d-lysine (1 mg/mL) (PDL, Sigma-Aldrich) was injected into the cell culture region and the devices were incubated at 37° C. for 1 hour and washed with DI (De- Ionized) water. Glutaraldehyde (0.1% (v/v)) (GA, Sigma-Aldrich) was then added and incubated for 1.5-2 hours at room temperature followed by washing the devices 4-5 times with DI water. Afterward, the devices were placed in the oven at 80° C. overnight to restore the hydrophobicity. Hydrophobicity enabled the microposts to contain the hydrogel within the culture regions prior to polymerization.

The device comprised the inner tumor region 301 and stromal regions 302, which are surrounded by the third vascular region 303. The diameter of the concentric circles were 1, 2 and 3 mm and the height of these concentric regions were 200 µm, respectively. The distance between the edge of the inner region and outer region was 1 mm. All three regions were bound by trapezoidal micro-posts 305 spaced evenly at 100 µm. The micro posts 305 were configured to separate the regions, while enabling the interactions between the regions by allowing exchange of media and movement of biomolecules and cells throughout the platform.

Cell Culture

Highly metastatic MDA-MB-231 (ATCC), non-invasive tumorigenic MCF7 breast cancer cells and Human umbilical vein endothelial cells (HUVEC) were primarily used for this study. MDA-MB-231 and MCF7 cells were transfected with a red dye. MDA-MB-231 and MCF7 cells were cultured in advanced DMEM (1× Dulbecco's Modified Eagle's Medium (DMEM) with 10% fetal bovine serum (FBS), 1% L-glutamine, and 1% 50:50 penicillin: streptomycin). Media supplements were purchased from Life Technologies. HUVECs were cultured in standard Endothelial Growth Medium (EGM-2). Cells were kept at a standard physiological condition (humidified, 37° C., 5% $CO_2$). Media was changed once after three days. Cells were cultured up to 70% confluency prior to passage or use for the experiments.

Invasion and Intravasation Assays

Firstly, MDA-MB-231 cells were dislodged from the culture flasks using trypsin-EDTA and were centrifuged and then suspended in collagen I (1.5 mg/mL, Corning® Collagen I, Rat Tail,) for a final cell density of 20 million cells/ml. The cell-hydrogel solution was mixed and then injected into the tumor region 301 of the device. The devices were then placed in the incubator (humidified, 37° C., 5% $CO_2$) for 20 minutes. Subsequently, collagen (1.5 mg/ml) was injected into the stroma region 302 followed by 20 minutes of incubation allowing hydrogel polymerization. As a control to compare the effect of invasive and non-invasive cell lines on vascularization; MCF7 cells were introduced into the tumor region 301 encapsulated in the collagen. Subsequently, HUVECs were disassociated from culture flasks using trypsin-EDTA and centrifuged. Fibrinogen solution was prepared by dissolving 5 mg/ml bovine fibrinogen in Dulbecco's phosphate buffered saline (DPBS) and thrombin solution was prepared by dissolving bovine thrombin in DPBS to get 4 U/ml thrombin solution. Both fibrinogen and thrombin solutions were filter sterilized. Fibrin solution (5 mg/ml fibrinogen and 4 U/ml Thrombin) was then added to get a hydrogel solution with the final cell density of 20 million cells/ml. The mixture was then immediately injected into the vascular region 303 of the device and the devices were kept at room temperature for 10 minutes for the fibrin to polymerize. After all hydrogel polymerization, a 70:30 ratio of EGM2 bullet kit (endothelial cell media) and cancer cell media (DMEM with FBS, L-glutamine, Penicillin, and streptomycin) was added to the media channels 304 of each device and the platforms were kept in the incubator (humidified, 37° C., 5% $CO_2$) for further biological studies. Media was exchanged every 24 hours throughout the cell culture period (6 days).

Immunofluorescence Staining

For immunofluorescence staining, the cells encapsulated in the hydrogel were fixed in 4% paraformaldehyde (PFA). Media within the platform was removed and 10 µl of 4% PFA were added to the wells and a gentle negative pressure was applied to the small well to even the flow. Devices were kept in the incubator (humidified, 37° C., 5% $CO_2$) for 30 minutes. After incubation, to permeabilize the cells, the samples were rinsed with PBS-glycine (100 mM glycine in PBS) 2 times with 10 minutes incubation at room temperature and washed with PBS-Tween-20 (PBS-Polyoxyethylene (20) sorbitan monolaurate) (0.05% (v/v) Polyoxyethylene (20) sorbitan monolaurate in PBS) for another 10 minutes at room temperature. Following permeabilization, to inhibit non-specific binding of antibodies, the cells were blocked with immunofluorescence buffer (IF buffer: (0.2% (v/v) polyethylene glycol p-(1,1,3,3-tetramethylbutyl)-phenyl ether, 0.1% (v/v) BSA (radioimmunoassay grade), 0.05% Polyoxyethylene (20) sorbitan monolaurate, and 7.7 mM $NaN_3$ in PBS). IF buffer plus goat serum (10% (v/v) goat serum) was added to the media channels and the devices were incubated at room temperature for 2 hours. To stain for endothelial cell-cell junction, primary antibody CD-31 (10 µg/ml, DHSB) was diluted in IF buffer and centrifuged at 14K RPM for 10 minutes to ensure optimum mixing. The mixture was then added to the blocked samples and kept at 4° C. overnight. Devices were kept in petri dishes and parafilmed to avoid evaporation. The next day, the devices were washed with IF buffer 3 times each with 20 minutes interval at room temperature. Then the secondary antibody (Alexa Fluor® 488) was diluted in an IF buffer and centrifuged at 14K RPM for 10 minutes. The mixture was added and the devices were incubated at room temperature for 3 hours. The devices were then washed once with IF buffer for 20 minutes followed by 2 times washing with PBS-Tween-20 for 10 minutes. Further, to counterstain for actin cytoskeleton and nucleus, Alexa Fluorx 488 Phalloidin (Invitrogen) (1:40) and 4', 6-diamidino-2-phenylindole (DAPI, Invitrogen) (1:1000) were added to the devices respectively. The devices were the kept at 4° C. overnight. Following staining, the devices were finally washed with PBS-Tween-20 three times each with 10 minutes intervals. Stained samples were imaged using fluorescence microscopy (Zeiss Axio Observer Z1 with the Zen Pro software suite) equipped with Apotome.2 (Zeiss) at 20× and 40× magnification. Z-stack images at 10×, 20×, and 40× magnification were obtained and, using the Zen software, 3D images were constructed.

Permeability Analysis

On day 6, upon formation and maturation of endothelial vascular networks within the third layer of the platform 303, fluorescent dye FITC-dextran (70KDa, 2.5 µg/ml diluted in EGM2 media, Invitrogen) was utilized to measure the diffusive permeability of the endothelial networks. Before introducing fluorescent dextran, the integrity of the vascular networks was confirmed using phase contrast microscopy. Media from the channels 304 was removed and 40 µl of dextran solution was added to the channels. A slight negative pressure was applied on the other side of the channel to even the flow. Devices were placed under the microscope and the flow of dextran solution was visualized. Next, sequential images were captured using the fluorescent microscope every 15 seconds for 30 minutes. Movement of dextran into and out of the vascular networks was observed using real time fluorescence microscopy. Images at t=0 and t=30 minutes were utilized to measure the fluorescence intensities of the vascular network in the regions of interest using NIH ImageJ software. Later, permeability of the vascular networks was measured using the following equation:

$$P_d = \frac{1}{\Delta I_i}\left(\frac{\Delta I_f}{\Delta t}\right)\left(\frac{d}{4}\right)$$

$P_d$ = Permeability $\Delta I_i = I_i - I_b y$ $\Delta I_f = I_f - I_i y$ where $I_b$, $I_i$, and $I_f$ are the background, initial, and final average intensities, respectively, $\Delta t$ is the time interval between images, and d is the diameter of the imaged microvessel.

Time-Lapse Imaging

Phase contrast and fluorescence images were acquired using Zeiss Axio Observer Z1 equipped with Apotome2 (Zeiss) and Zen Pro software. Throughout the cell culture period, phase contrast images were taken every day at 10× objective using 4×3 tiles. Immunofluorescent images were obtained with 10×, 20× and 40× objectives and Z-stacked images were captured to construct the 3D images. Time-lapse imaging of MDA-MB-231 during invasion and intravasation was performed using a custom-built incubator assembled on the microscope. The microfluidic devices were placed inside a miniature incubator (TC-MWP, Bioscience Tools) at 37° C. and 5% $CO_2$. Movies were recorded for at least 12 hours overnight.

Quantification of Angiogenic Factors within the Microengineered Model

Conditioned medium from the invasion and intravasation assay was collected daily for six days and pooled together to profile secreted factors across the culture period. We analyzed secreted factors from mono-culture conditions of MDA-MB-231 and HUVECs as well as the co-culture of these cells. An angiogenesis enzyme-linked immunosorbent assay (ELISA, QAH-ANG-1-1, Raybiotech) was utilized to quantify angiogenin, angiopoietin-2 (ANG-2), epidermal growth factor (EGF), basic fibroblast growth factor (bFGF), heparin-bound–EGF (HB-EGF), hepatocyte growth factor (HGF), Leptin, platelet-derived growth factor (PDGF-BB), placenta growth factor (P1GF), vascular endothelial growth factor A (VEGF-A) per manufacturer's instruction. In addition, to improve detection of the cytokines, we diluted the conditioned media in the sample diluent at ratio of (1:3).

Data Collection and Statistical Analysis

To quantify the number of invading cancer cells, both phase contrast and fluorescent images were utilized. Specifically, on day 2 of culture phase contrast images with 10× objective were used, while for days 4 and 6 of culture, fluorescent images of samples stained for actin and nucleus were used. Images were processed (i.e. thresholded) using an extended particle analyzer plugin of the NIH ImageJ software and the number of cells was counted. To quantify cancer cell morphology, fluorescent images of the samples on day 4 and 6 were used. Images were processed using ImageJ software and extended particle analyzer software plugin was used to quantify the cell morphology, specifically the cell circularity, aspect ratio, and roundness. To visualize the intravasation of cancer cells in the outer vessel capillaries, fluorescent images of red-expressing MDA-MB-231 cells with 20× and 40× magnification were captured.

To analyze vascular network morphology, including branching and diameter of the vessels, fluorescent images of samples, stained for endothelial junction markers CD31 captured on days 2, 4, and 6, were used. Images were processed using the NIH ImageJ and the diameters of the vascular networks were measured by drawing a line through one point to another of the vascular network. Measure plugin of the ImageJ was used to measure the length of the line to yield the diameter values.

For the entire analysis, all the values were obtained over a course of 3 independent experiments (n=3). Each experiment had 2-3 technical replicates. The data were analyzed with the unpaired Student's t-tests. Multiple comparisons tests were performed within the GraphPad Prism software (GraphPad Prism 6).

Optimization of the Vasculogenesis Process within Fibrin Matrix

To study vasculogenesis and to optimize the ECM composition for endothelial cell sprouting, we first developed a microfluidic model comprised of a single culture region surrounded by the media region. This device was selected to study endothelial growth without the interference of other cell types or the stroma. Since the media channel is in a different compartment from the cell culture region, it facilitated the development of a gradient of biomolecules. To encapsulate endothelial cells fibrin was chosen, as it is known to play a major role in regulating angiogenesis in 3D ECM. Endothelial cells (HUVECs) at a cell density of 20 million cells/ml were injected into the devices and growth and maturation of vascular networks were monitored over a culture period of 5 days. We introduced vascular endothelial growth factor (VEGF) in to the culture media and assessed the subsequent effects on vasculogenesis. VEGF is known as a major growth factor secreted during cancer progression which leads to formation of new blood vessels. In the control experimental group (No VEGF), intercellular connections were mainly absent across the culture period. However, in low and high VEGF conditions, endothelial cells showed elongated morphology with intercellular connections from day 1. Vascular networks were developed with tube-like structures on day 3. The formed networks further matured with interconnected cellular clusters covering the entire culture region by day 5. We primarily compared the diameter and branching of vascular networks and further assessed the permeability of microvessels within each experimental condition. The results showed that endothelial networks formed under the influence of VEGF were impaired structurally and had higher permeability. This preliminary study demonstrated successful formation of 3D capillary networks within the fibrin gel.

Specification of the Three-Layer Platform and Experimental Conditions

We further intended to introduce a tumor region 301 and stroma region 302 within the microfluidic platform 300 to study the interaction of cancer and endothelial cells on invasion, intravasation and vasculogenesis through the crosstalk between the cell types. As such, we further modified the microfluidic platform discussed above into three layer device, incorporating tumor 301, stroma 302, and vascular 303 regions (see FIG. 10). The three-layer microfluidic platform 300 enabled us to spatially organize the three important components including tumor, stroma and vasculature side-by-side in different regions, while maintaining their interconnectivity and allowing diffusion of biomolecules and dynamic heterotypic interactions in between the regions. Following the fabrication of the platform 300, the next focus was to optimize the ECM composition within each region. For the tumor region 301, encapsulated with cancer cells, as well as the middle stromal layer 302, collagen was selected as it constitutes the major protein within tumor microenvironment ECM. Concentration of collagen was first optimized and a final concentration of 1.5 mg/ml was used for experiments. We also optimized the tumor cell density, and the preliminary experiments indicated that 20 million cells/ml was optimum to form a solid dense tumor and observe cancer cell migration. Upon injection of the tumor region 301 and stromal region 302, endothelial cells embedded in a fibrin hydrogel was loaded into the third scaffold 302 of the device. The fibrin matrix was similar to those that optimized in one layer devices as discussed above. The platform 300 had a media channel 304 surrounding the three entities filled with the media. This allowed for diffusion of media and the creation of a gradient of biomolecules throughout the platform passing the vascular region 303 and then toward the stromal region 302 and tumor scaffold 301.

Analysis of Cancer Cells Invasion within the Stroma Region

To gain a primary insight on the dynamics of tumor-endothelial cell interactions, we first tracked the migration pattern of the cancer cells. 3D z-stack images were acquired every 24 hours to monitor cancer cell invasion dynamics. By day 1, MDA-MB-231 cells started to disseminate from the primary tumor region and invaded into the stromal region.

Figure 11:
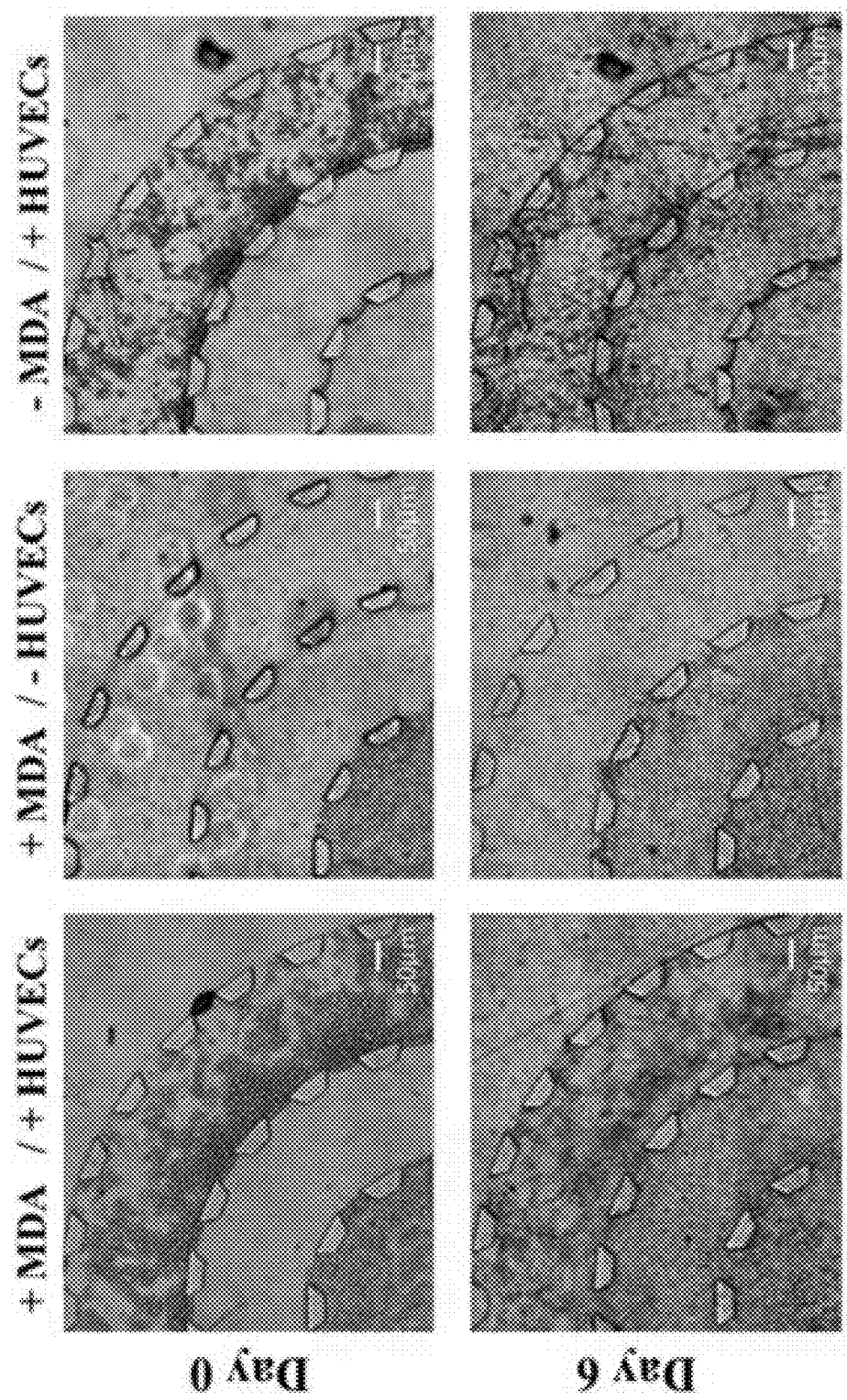
FIG. 11 is a series of photographs showing the progress of cancerous and endothelial cells over time within a section of the third exemplary microfluidic device. The progress with cancer cells and endothelial cells (+/+ MDA/HUVECS) is the first column, with cancerous cells and without endothelial cells (+/− MDA/HUVECS) is the second column, without cancerous cells and with endothelial cells (−/+ MDA/HUVECS) is the third column.
Figure 12:
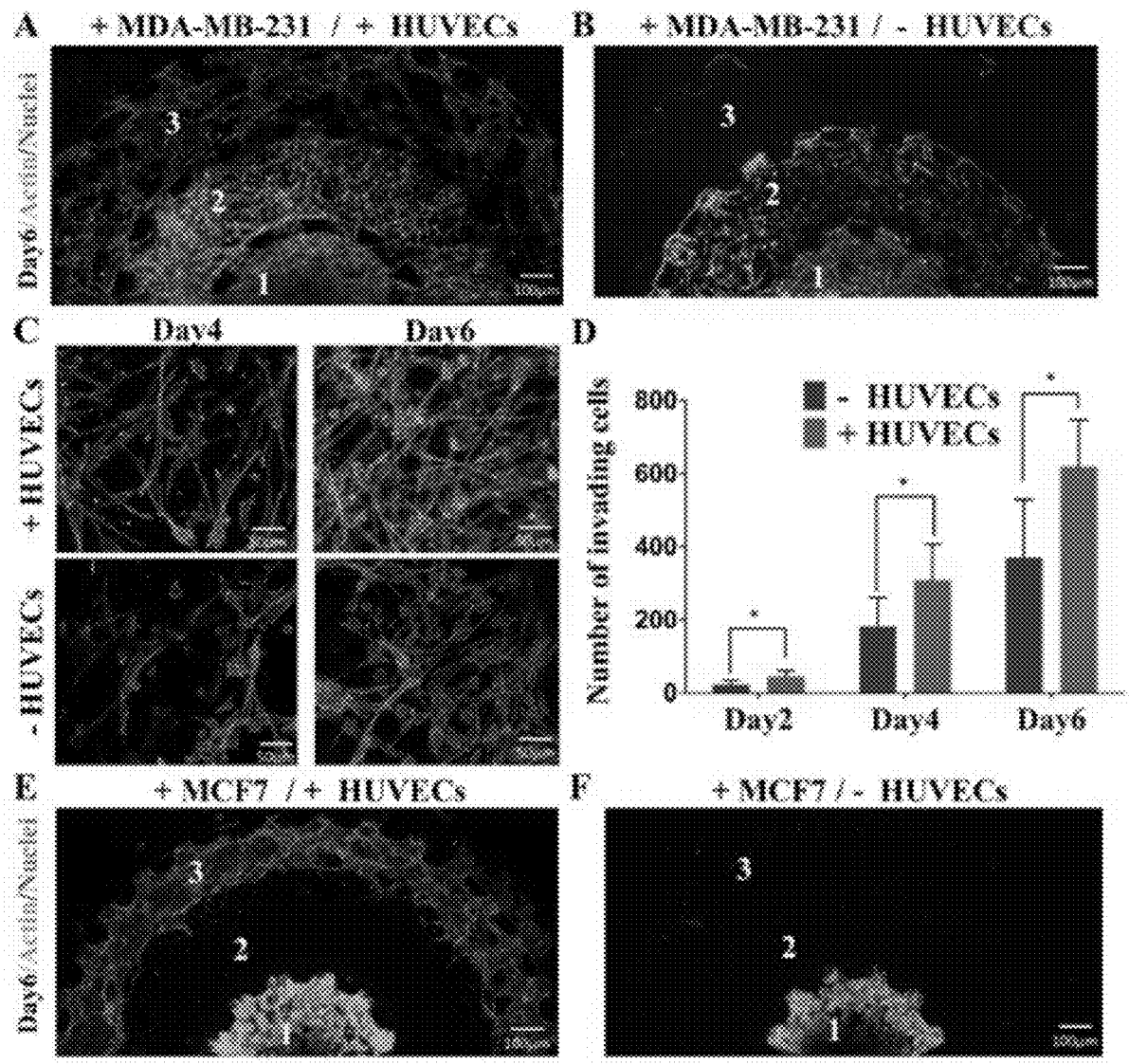
FIG. 12 is a number of related photographs and a graph showing the characterization of the cancer cells invading the stroma within a section of the third exemplary microfluidic device. Photographs A-C are representative fluorescent images of the entire culture region on day 6 (1: Tumor, 2: Stroma, 3: Vascular) and demonstrate cancer cell invasion through the stroma on days 4 and 6 of culture. Photographs in C are representative of cancer cells invading the stroma on days 4 and 6 of culture. Graph D is a quantitative analysis of the number of cancer cells invading the stroma (*denotes a significant difference for p<0.05). Photographs E and F are representative fluorescent images of the MCF7 (control condition) on day 6 (1: Tumor, 2: Stroma, 3: Vascular).

As can be seen in FIG. 11 and FIG. 12, the number of tumor cells in the stromal region increased over time regardless of the presence of an endothelial microvascular networks within the third layer. As shown by FIG. 12, by day 2, the number of cells in the stromal region was relatively low, therefore we could count the number of cells (−HUVECs: 22.7±11.9, +HUVECs: 45.5±15.2) through the phase contrast imaging. By day 4 (−HUVECs: 181.3±79.5, +HUVECs: 309.0±98.4) and day 6 (−HUVECs: 370.2±159.2, +HUVECs: 618.3±129.3), as the number of invading cells increased drastically, we stained the cell nuclei with DAPI to quantify the number of invading cells within specific ROIs (Images C and D). We compared the number of invading cells between the two conditions, namely in presence and absence of vascular networks made up of HUVECs. We found that in the presence of vascular networks, the number of cells invading the stroma was significantly higher than the number of cells invading in control conditions without the presence of endothelial networks (Image D). This suggested that the presence of endothelial cells promoted cancer cell invasiveness into the stroma. We further analyzed the morphology of MB-MDA-231 cells invading into the stroma (Images A and B). From the preliminary phase-contrast images, we could observe that the cancer cells in the presence of vascular network exhibited elongated morphologies with more protrusions. Further observation of the immunofluorescence Z-stack images of the actin cytoskeleton also confirmed the elongated morphology of the tumor cells. On the contrary, the less invasive MCF7 cells did not invade into the stromal region. We could observe that even in the presence of vascular networks, MCF7 cells did not enter the adjacent stroma region; rather they were restricted and clustered within the tumor region (Images E and F).

Cancer Cell Intravasation into the Endothelial Vessel Networks

Figure 13:
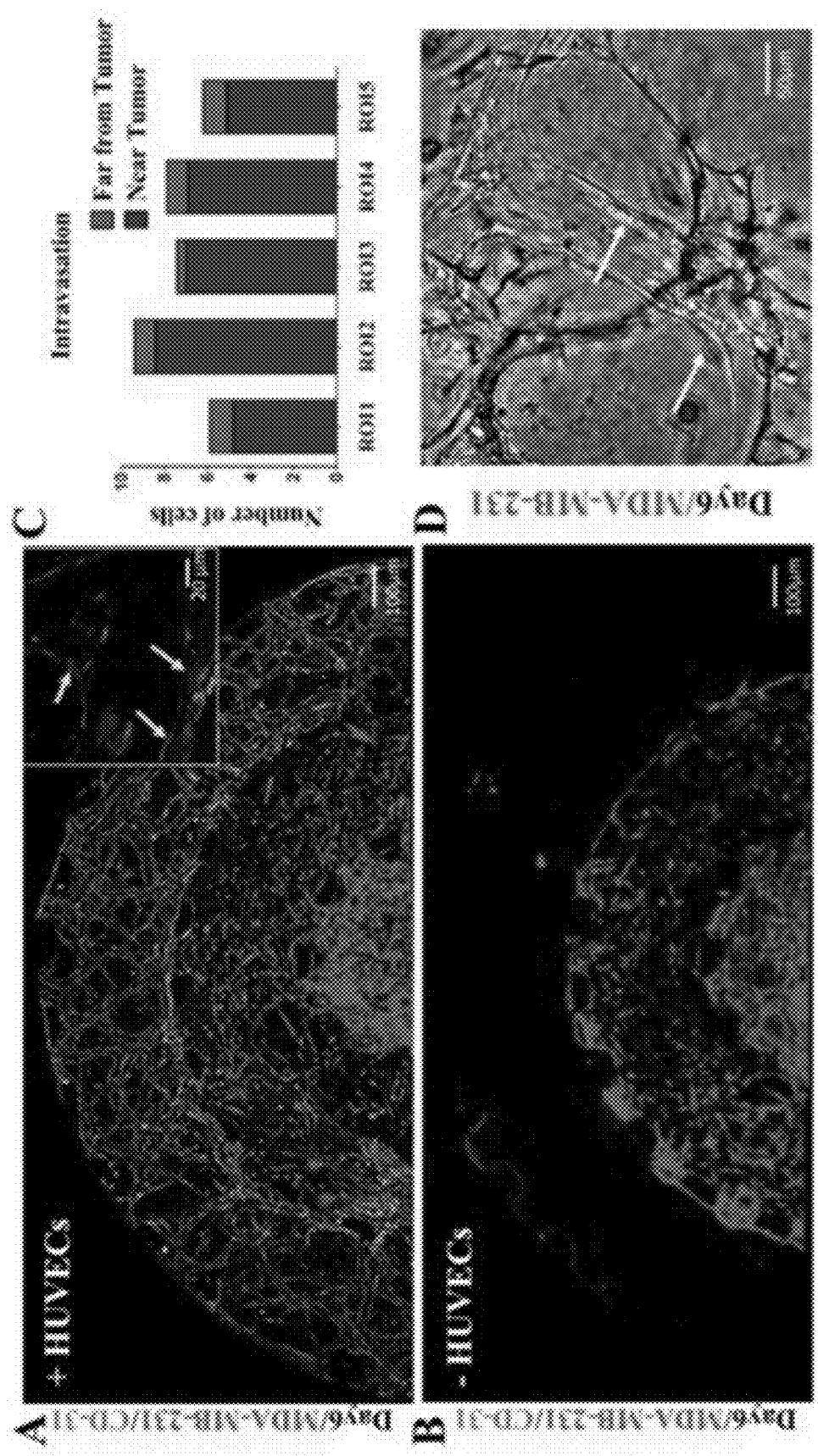
FIG. 13 is a number of related photographs and a graph showing the intravasation of cancer cells into the vascular network within a section of the third exemplary microfluidic device. Photograph A is a representative fluorescent image of cancer cells intravasation into the vascular network on day 6. Yellow arrows within the inset denote presence of MDA-MB-231 cells in the vascular region. Photograph B is a representative fluorescent image without HUVECs showing that cancer cells stay within the stromal region on day 6. Photograph C and its accompanying graph show the quantitative number of cancer cells, in the different regions of interest within the platform, intravasating into basal and apical regions of the vascular network. Photograph D is a real-time phase contrast image of cancer cell entering the vascular region. MDA-MB-231 cells are fluorescently labeled red.

Intravasation is the migration of tumor cells into the endothelial networks and vascular lumen by crossing the endothelial barriers. We hypothesized that the presence of the endothelial network, within the third layer of our platform, would cause highly invasive cancer cells to successfully enter (i.e. intravasate) into the surrounding vascular network, as illustrated in the images and graph of FIG. 13. To characterize the ability of cancer cells to invade the 3D endothelial network, high-resolution images were acquired for tomato-expressing MDA-MB-231 cells, while endothelial cells were stained in green for CD31 cell-cell junction proteins (Image A). From this image, we were able to observe MDA-MB-231 cells entered the vascular region on day 6 (yellow arrows of inset in Image A). We also found that in the control condition without the presence of vascular networks, MDA-MB-231 cells did not migrate into the fibrin matrix (Image B).

From real-time imaging of cancer cell invasion in presence of the formed vascular network, we could visualize MDA-MB-231 cells elongating and forming protrusions when crossing into the vascular layer 303 (white arrows in Image D). To quantify the number of intravasating tumor cells, we counted the number of cells that entered into the vascular region. Therefore, five ROIs were marked throughout the vascular region of the device and each region was divided into two equal halves to test for the distribution of invading MDA-MB-231 cells within the vascular region. Based on the distribution of invasion, the obtained results showed that many of the cancer cells were found at the front half of the vascular region. Fewer number of cells migrated and reached the rear half of the vascular network within the culture period (day 6). Notably, the distribution of tumor cells in the ROIs was consistent throughout the whole vascular region (Image C).

Characterization of Formed Vascular Networks

To investigate the effects of the presence of the tumor entity (first layer, 301), embedded with cancer cells, on growth and maturation of endothelial network within the third layer 303 of the platform, we studied the morphology of the formed vasculature in presence (+MDA) and absence of tumor (−MDA, control) by staining for actin cytoskeleton. The immunofluorescent images demonstrated the formation of well-formed, well-connected vascular networks in both conditions. However, we could observe significant changes in the morphology of the vascular networks in the presence of the MDA-MB-231 cells. We measured the diameter of randomly chosen vessels visualized by the actin cytoskeleton (white arrows in FIG. 14, Images A and B). We found that the vessels in presence of MDA-MB-231 cells exhibited significantly lower diameter (41.15±13.8 μm) compared to diameter of vessels in the control conditions (77.35±34.26 μm) (Image C). These results also were in agreement with the endothelial cell mono-culture studies within the single layer platform, in which the diameter of the formed vascular networks was reduced due to addition of VEGF within the microenvironment.

Conversely, in the presence of MCF7 cells, the morphology of the endothelial networks formed did not demonstrate any significant changes, in terms of vascular network diameter, as compared to the control condition without the presence of MCF7 cells in the tumor entity (Images B and D).

Permeability of the Vascular Networks

Figure 14:
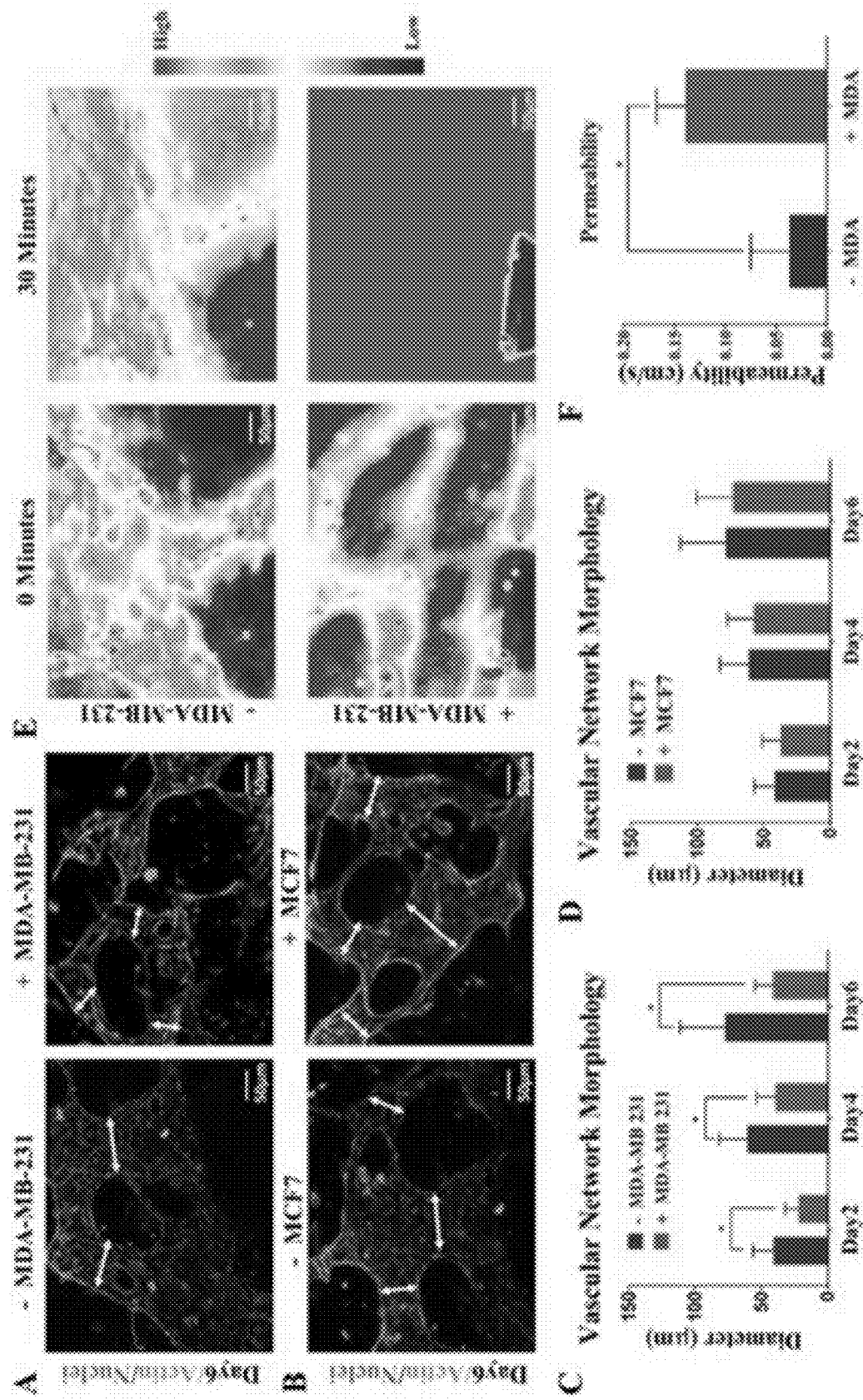
FIG. 14 is a number of related photographs and graphs characterizing the morphology of the vascular network within a section of the third exemplary microfluidic device. Photographs A and B are representative fluorescent images of the vascular network on day 6 of culture of MDA-MB-231 and MCF7. White arrows denote distance between vessel walls. Graphs C and D show quantification of the diameter of the vascular network in presence of MDA-MB-231 and MCF7. Graph E shows the heatmap of fluorescence intensity denotes diffusion of FITC-dextran. Blue is low and red is high intensity correlating to concentration. After 30 minutes in the presence of MDA-MB-231, vascular networks demonstrated leakage of FITC-dextran throughout the platform suggesting enhanced permeability. Graph F shows quantified permeability values of the endothelial region(*denotes a significant difference for $p<0.05$).

To address the question of whether tumor cells resulted in formation of leaky vascular network, we conducted permeability measurements of endothelial networks under mono-culture and co-culture conditions (with and without MDA-MB-31). Fluorescently labeled dextran was dissolved into the culture media (70 KDa, 2.5 µg/ml) and injected into the media channels of the devices. In presence of MDA-MB-231, the vascular networks were observed to be more permeable as there was enhanced leakage of dextran into the perivascular region, leading to reduced fluorescent intensity in the vascular region (FIG. 14, Image E). In the absence of tumor (−MDA, control) fluorescent intensity within the endothelial network was significantly higher, confirmed the formation of less permeable networks. The permeability value for in presence of MDA-MB-231 was 0.1385±0.028 cm/s which was significantly higher than the control (−MDA, 0.03637±0.038 cm/s) (Image F). These findings suggest that tumor cells perturb endothelial network function by making them to be more permeable and leaky. This was indeed consistent with our results obtained in single layer device with mono-culture of endothelial cells, suggesting that higher permeability of vascular networks in presence of invasive cancer cells might be due to enhanced secretion of VEGF.

Figure 15:
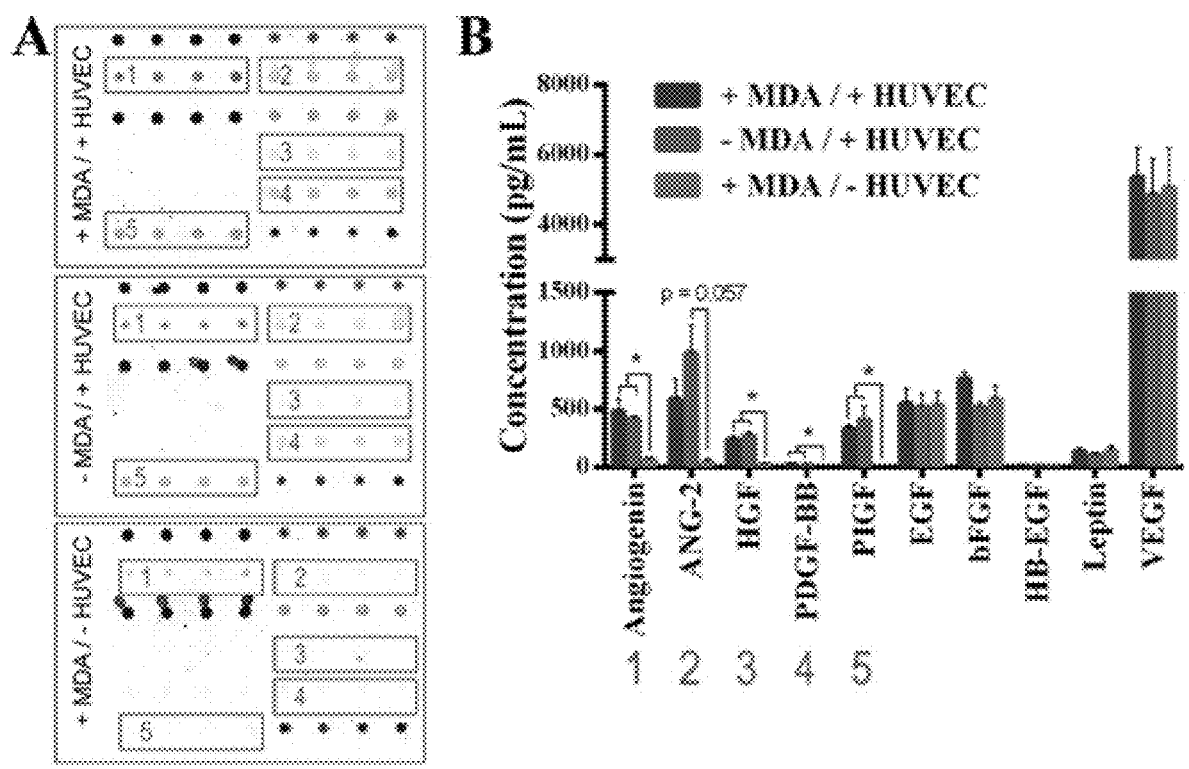
FIG. 15 is a number of related photographs and a graph showing characterization of the secreted cytokines within the conditioned medium of the third exemplary microfluidic device. The photographs in A show a representative cytokine blot from the antibody array of the angiogenic factors (1: Angiogenin, 2: ANG-2, 3: HGF, 4: PDGF-BB, 5: P1GF, red boxes indicate difference in fluorescent intensity among the conditions). Graph B shows a quantification of secreted factors (*denotes a significant difference for $p<0.05$).

Profiling the Secreted Signaling Molecules within the Tumor-Vascular Microenvironment To examine the cytokine profile of the tumor vascular microenvironment that governed the changes we observed in migration and vascular morphology, we utilized an ELISA array (Raybiotech) to detect and quantify the concentrations of 10 angiogenesis-related cytokines including, Angiogenin, ANG-2, EGF, bFGF, HB–EGF, HGF, Leptin, PDGF-BB, P1GF, VEGF-A. We profiled the secreted factors within the conditioned medium from mono-cultures of MDA-MB-231 and HUVECs as well as the co-culture condition within the microfluidic device (FIG. 15, Image A). From the results (Table in FIG. 16), we observed a notable amount of VEGF (>5000 pg/mL) detected compared to the other factors. Additionally, there was low detection of HB–EGF (<6 pg/mL) within all the conditions. Further analysis revealed that six of the ten secreted proteins analyzed showed no significant difference (FIG. 15, Image B). However, angiogenin, HGF, PDGF-BB, and P1GF showed a significant increase when HUVECs were present within the vascular region of the platform corresponding to the images of the array (red boxes in Image A). We did not detect a significant influence in cytokine profile between the co-culture and HUVEC mono-culture (red boxes in Image A). This suggests that these signaling molecules are mainly secreted by HUVECs as we also confirmed that they were not present within the media through the ELISA array as well as the EGM-2 Bullet Kit datasheet. In addition, HGF, PDGF-BB, and P1GF are known cytokines[18-20] that are involved in enhancing cancer invasion which we detected in the MDA-MB-231 and HUVEC co-culture (Image B). We further utilized unsupervised clustering showing that the mono-culture of HUVECs clustered with the co-culture condition separately from mono-culture of MDA-MB-231 cells. This again suggests that presence of HUVECs had a greater influence on the secreted factors.

Discussion

In this work, we present a unique microfluidic in vitro model comprising of three distinct, but interconnected layers. This enabled spatial organization and compartmentalization of tumor, stroma and endothelial entities. Geometry and design enabled side-by-side arrangement of the tumor and stromal components in the 3D matrix, and it also incorporated diffusive barriers for transport of nutrients and growth factors thereby enabling bi-directional crosstalks between the different layers, specifically cancer and endothelial cells. Compared to other in vitro models for invasion and intravasation, our model presents various advantages in developing comprehensive assays such as (i) The well-formed solid tumor surrounded by stroma allowed modeling of the cancer invasion from the primary tumor to a stromal region in response to secreted biomolecules. This further allowed us to quantify the number as well as the morphology of the invading cancer cells. (ii) Most importantly, having separated but interconnected compartments for tumor and endothelial cells enabled studying both the cancer cell behavior and vasculogenesis simultaneously. We could observe spontaneous growth and maturation of vascular networks and quantify the morphological characteristics of the endothelium in response to cancer cell signaling. The architecture of the model also enabled permeability studies on mature microvessels and helped us elucidate the changes in permeability of the formed vasculature due to tumor-endothelial interactions. (iii) Both cancer and endothelial cells were embedded in 3D matrices, facilitating cell-cell and cell-ECM interactions mimicking the 3D complex tumor microenvironment. (iv) This developed model was also capable of obtaining the dynamics of tumor-endothelial interactions during cell invasion and intravasation in a real-time fashion at a single cell level. (v) Lastly, we collected the conditioned media from the developed platform and produced a cytokine profile in order to understand the governing factors in cancer cell migration and changes in vascular morphology.

Our working model is that the cross talk between tumor and endothelial cells are crucial during cancer progression. We know from previous studies that endothelial cells affect tumor cell behavior with respect to morphology and the invasive characteristics and in turn the cancer cells secrete several biochemical factors which modify the vascular network morphology, which facilitates tumor cell intravasation. Consistent to these studies, our findings showed that significantly higher number of cancer cells invaded the stromal region in the presence of endothelial vascular networks. Our analysis further revealed that cancer cells in the stroma showed elongated shape with more protrusions in the presence of the vascular network as compared to cancer cells in the absence of the vascular network. Our results are also in accordance with previous in vivo studies suggesting that number of invading and circulating tumor cells increases in the presence of vascular networks. These results also suggest that endothelial cells exert pro-metastatic characteristics where cancer cells are attracted to vascular network with a more invasive (i.e. aggressive) phenotype. By day 6 in culture, cancer cells crossed endothelial barrier and entered the vascular region through passive intravasation. The unique ability within our platform to image the dynamics of tumor endothelial interactions enabled us to visualize in real-time the process of intravasation. Interestingly, the presence of endothelial cells did not did not induce any migratory pattern of MCF7 cells, where they were bound within the tumor region and did not migrate into even the stromal region.

Our findings further demonstrated that vascular networks were thinner with reduced diameter with significantly higher permeability in presence of the tumor entity embedded with highly metastatic cancer cells. The results are in accordance with endothelial mono-culture studies within the one-layer platform, where the diameter of the vasculature decreased and permeability increased due to presence of increased levels of VEGF. Taken together the results suggest that the cancer cells secrete biomolecules such as VEGF, which modulate the morphology and the permeability of the surrounding tumor vasculature.

In conclusion, our overall findings demonstrated that our developed microfluidic platform can be employed to study tumor growth, cancer cell invasion, and intravasation on a single platform and to unveil mechanistic biological insights within each separate stage of the metastatic cascade within a well-controlled (i.e. cell-cell and cell-ECM interactions) microenvironment. We showed that in the presence of a vascular network, MDA-MB-231 cells responded by enhanced invasion and intravasation while MCF7 cells did not migrate. On the other hand, MDA-MB-231 influenced the vascular morphology by decreasing vascular network diameter and permeability. In addition, we analyzed the conditioned media from the assay and identified possible cytokine candidates involved in the tumor vascular cross-talk. Thus, the proposed platform has potential to be a valuable tool to study cancer behavior and recapitulate the interactions of tumor and endothelial cells. We envision that the platform can be used for screening drug targets and to develop personalized medicine.

The present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A microfluidic device, comprising:
    a surface defining one or more microfluidic channels, wherein the surface extends beyond the one or more microfluidic channels;
    a first three dimensional scaffold comprising one or more cancer cells that is spatially separated from the one or more microfluidic channels;
    a second three dimensional scaffold, at least a portion of which is contacting and in fluid communication with the first three dimensional scaffold, and that is spatially separated from the one or more microfluidic channels; and
    a third three dimensional scaffold, at least a portion of which is contacting and in fluid communication with the one or more microfluidic channels and the second three dimensional scaffold, wherein the extended surface underlies the first, second and third three dimensional scaffolds.

2. The microfluidic device of claim 1, wherein the one or more cancer cells are metastatic or tumorigenic cancer cells.

3. The microfluidic device of claim 1, wherein the one or more cancer cells are breast cancer cells.

4. The microfluidic device of any of claim 1, wherein the second three dimensional scaffold comprises one or more stromal cells.

5. The microfluidic device of claim 4, wherein the one or more stromal cells are fibroblasts.

6. The microfluidic device of claim 1, wherein the second three dimensional scaffold comprises one or more macrophages.

7. The microfluidic device of claim 1, wherein the third three dimensional scaffold comprises one or more endothelial cells.

8. The microfluidic device of claim 1, wherein the one or more of the microfluidic channels comprises one or more growth factors.

9. The microfluidic device of claim 1, wherein at least one of the first three dimensional scaffold, the second three dimensional scaffold, and the third three dimensional scaffold comprise a gel matrix.

10. The microfluidic device of claim 9, wherein the gel matrix comprises one or more of the group consisting of collagen, fibronectin, fibrinogen, hyaluronan, a hydrogel, a peptide gel, a gel-like protein or interpenetrating network hydrogels.

11. The microfluidic device of claim 9, wherein the gel matrix comprises a collagen hydrogel.

12. The microfluidic device of claim 8, wherein the surface extends beyond the one or more microfluidic channels defined thereby, and wherein the extended surface underlies both the first, second, and third three dimensional scaffolds.

13. The microfluidic device of claim 12, wherein the surface further comprises microposts separating at least one of the first three dimensional scaffold, the second three dimensional scaffold, the third three dimensional scaffold, and the one or more microfluidic channels along the portion that contacts.

14. The microfluidic device of claim 1, further comprising one of more inlets for adding at least one of the first three dimensional scaffold, the second three dimensional scaffold, and the third three dimensional scaffold to the microfluidic device.

15. The microfluidic device of claim 1, wherein one or more of the microfluidic channels comprises one or more fluidic inlets suitable for introducing a test agent into the microfluidic device.

16. The microfluidic device of claim 14, wherein the one or more microfluidic channels comprises a first microfluidic channel on a first side of the third three dimensional scaffold and a second microfluidic channel on an opposite second side of the third three dimensional scaffold.

17. The microfluidic device of claim 1, wherein the one or more cancer cells are obtained directly from a cancer patient in need of treatment.

18. The microfluidic device of claim 5, wherein the fibroblasts are obtained directly from a cancer patient in need of treatment.

19. The microfluidic device of claim 6, wherein the one or more macrophages are obtained directly from a cancer patient in need of treatment.

20. The microfluidic device of claim 7, wherein the one or more endothelial cells are obtained directly from a cancer patient in need of treatment.

21. A method of assaying a test agent for anti-cancer activity, comprising:
    introducing the test agent to the microfluidic device of claim 15 through the one or more fluidic inlets; and observing the cancer cells within the microfluidic device to determine the effect of the test agent.

22. The method of claim 18, wherein the cancer cells are obtained directly from a patient in need of treatment or commercially available cells lines.

23. A method of studying cancer or related cells, comprising:
observing one or more of the cancer cells or related cells within the microfluidic device of claim 1.

24. The method of claim 20, further comprising the steps of altering one or more microenvironments within the microfluidic device and determining the effect of the alteration on the one or more cancer cells or related cells.

* * * * *